(12) United States Patent
Liu et al.

(10) Patent No.: US 9,814,709 B2
(45) Date of Patent: Nov. 14, 2017

(54) BRUTON'S TYROSINE KINASE INHIBITOR

(71) Applicants: HEFEI INSTITUTES OF PHYSICAL SCIENCE, CHINESE ACADEMY OF SCIENCES, Anhui (CN); ANHUI NEW STAR PHARMACEUTICAL DEVELOPMENT CO., LTD, Anhui (CN)

(72) Inventors: Qingsong Liu, Hefei (CN); Jing Liu, Hefei (CN); Yongfei Chen, Hefei (CN); Hong Wu, Hefei (CN); Aoli Wang, Hefei (CN); Beilei Wang, Hefei (CN); Chen Hu, Hefei (CN); Wenchao Wang, Hefei (CN); Cheng Chen, Hefei (CN)

(73) Assignees: HEFEI INSTITUTES OF PHYSICAL SCIENCE, CHINESE ACADEMY OF SCIENCES, Hefei, Anhui Province (CN); ANHUI NEW STAR PHARMACEUTICAL DEVELOPMENT CO., LTD., Anhui Province (CA)

( * ) Notice: Subject to any disclaimer, the term of this patent is extended or adjusted under 35 U.S.C. 154(b) by 0 days.

(21) Appl. No.: 15/320,120

(22) PCT Filed: Jan. 27, 2015

(86) PCT No.: PCT/CN2015/071594
§ 371 (c)(1),
(2) Date: Dec. 19, 2016

(87) PCT Pub. No.: WO2015/192658
PCT Pub. Date: Dec. 23, 2015

(65) Prior Publication Data
US 2017/0128439 A1    May 11, 2017

(30) Foreign Application Priority Data

Jun. 20, 2014  (CN) .......................... 2014 1 0280931

(51) Int. Cl.
*A61K 31/4745*    (2006.01)
*C07D 471/04*    (2006.01)

(52) U.S. Cl.
CPC ........ *A61K 31/4745* (2013.01); *C07D 471/04* (2013.01)

(58) Field of Classification Search
None
See application file for complete search history.

(56) References Cited

U.S. PATENT DOCUMENTS 6,326,469 B1    12/2001    Ullrich et al.

FOREIGN PATENT DOCUMENTS

| WO | WO 2010/044885 A2 | 4/2010 |
|---|---|---|
| WO | WO 2013/154778 A1 | 10/2013 |
| WO | WO 2014/063054 A1 | 4/2014 |
| WO | WO 2014/145857 A1 | 9/2014 |

OTHER PUBLICATIONS

Jefferies C.A. et al., "Bruton's Tyrosine Kinase is a Toll/Interleukin-1 Receptor Domain-Binding Protein That Participates in Nuclear Factor kB Activation by Toll-Like Receptor 4", The Journal of Biological Chemistry 278 (28)26258-26264 (Jul. 11, 2003).
Kurosaki T., "Functional Dissection of BCR Signaling Pathways", Current Opinion in Immunology 12:276-281 (2000).
Liu F. et al., "Discovery of a Selective Irreversible BMX Inhibitor for Prostate Cancer", ACS Chemical Biology 8:1423-1428 (2013).
Quek L.S. et al., "A Role for Bruton's Tyrosine Kinase (Btk) in Platelet Activation by Collagen", Current Biology 8:1137-1140 (1998), and Supplementary Material.
Schaeffer E M et al., "Tec Family Kinases in Lymphocyte Signaling and Function", Current Opinion in Immunology 12:282-288 (2000).
Vassilev A. et al., "Bruton's Tyrosine Kinase as an Inhibitor of the Fas/CD95 Death-Inducing Signaling Complex", The Journal of Biological Chemistry 274(3):1646-1656 (Jan. 15, 1999).
GenBank Accession No. NP_000052.1 (6 pages) (Oct. 6, 2016).
GenBank Accession No. AAB47246.1 (3 pages) (Aug. 9, 2000).
GenBank Accession No. XP_549139.2 (3 pages) (Sep. 17, 2015).

(Continued)

*Primary Examiner* — Brian J Davis
(74) *Attorney, Agent, or Firm* — Scully, Scott, Murphy & Presser, P.C.

(57) ABSTRACT

The present invention provides a Bruton's tyrosine kinase inhibitor, which is a compound represented by formula (I) or a pharmaceutically acceptable salt, solvate, ester, acid, metabolite or prodrug thereof. The present invention also provides a pharmaceutical composition comprising the compound. The present invention also provides a method and use of using the Bruton's tyrosine kinase inhibitor to inhibit the tyrosine kinase activity or treat diseases, disorders or symptoms benefiting from the inhibition of the Bruton's tyrosine kinase (Btk) activity.

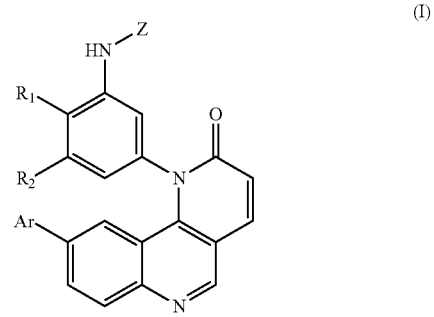

(I)

13 Claims, 5 Drawing Sheets

(56) References Cited

OTHER PUBLICATIONS

GenBank Accession No. NP_001007799.1 (4 pages) (Mar. 2, 2017).
GenBank Accession No. NP_989564.2 (5 pages) (Nov. 6, 2016).
GenBank Accession No. XP_698117.2 (2 pages) (Feb. 16, 2007).
International Search Report dated Jan. 21, 2016 received in Chinese Patent Application No. 201410280931.1, together with an English-language translation.
Chinese Office Action dated Jan. 29, 2016 received in Chinese Patent Application No. 201410280931.1, together with an English-language translation.
Chinese Office Action dated Jul. 25, 2016 received in Chinese Patent Application No. 201410280931.1, together with an English-language translation.
International Search Report dated May 4, 2015 issued in PCT/CN2015/071594.

BRUTON'S TYROSINE KINASE INHIBITOR

FIELD OF THE INVENTION

The present application relates to compounds used as inhibitors of Bruton's tyrosine kinase (Btk), pharmaceutical compositions comprising the compounds, as well as methods and uses for using these compounds and compositions to inhibit the activities of tyrosine kinases.

BACKGROUND OF THE INVENTION

Bruton tyrosine kinase is a member of the Tec family of non-receptor tyrosine kinases. It consists of a PH domain, a TH domain, a SH3 domain, a SH2 domain, and a catalytic domain. Btk is involved in a variety of signaling pathways, plays an important role in regulation of cell proliferation, differentiation and apoptosis. In addition, Btk is a key signal kinase expressed in all hematopoietic cell types except T lymphocytes and natural killer cells. Moreover, Btk plays a critical role in B cell signaling pathways that stimulate cell-surface B-cell receptor (BCR) stimulation to downstream intracellular responses.

Btk is a key regulator of B-cell development, activation, signaling, arid survival (Kurosaki, *Curr Op Imm*, 2000, 276-281; Schaeffer and Schwartzberg, *Curr Op Imm*, 2000, 282-288). In addition, Btk plays a role in a number of other hematopoetic cell signaling pathways, such as Toll like receptor (TLR) and cytokine receptor-mediated TNF-a production in macrophages, IgE receptor (FcεRI) signaling in Mast cells, inhibition of Fas/APO-1 apoptotic signaling in B-lineage lymphoid cells and collagen-stimulated platelet aggregation. See, e.g., C. A. Jeffries, et al., (2003), *Journal of Biological Chemistry* 278: 26258-26264; Vassilev et al. (1999), *Journal of Biological Chemistry* 274(3): 1646-1656; and Quek et al. (1998), *Current Biology* 8(20): 1137-1140.

SUMMARY OF THE INVENTION

The present invention relates to inhibitors of Bruton's tyrosine kinase. In particular, the compounds of the invention comprise the compounds of formula (I), pharmaceutically acceptable salts, solvates, esters, acids, metabolites or prodrugs thereof:

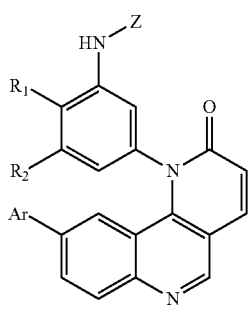

(I)

wherein, Ar is selected from the group consisting of aryl and heteroaryl;

Z is selected from the group consisting of

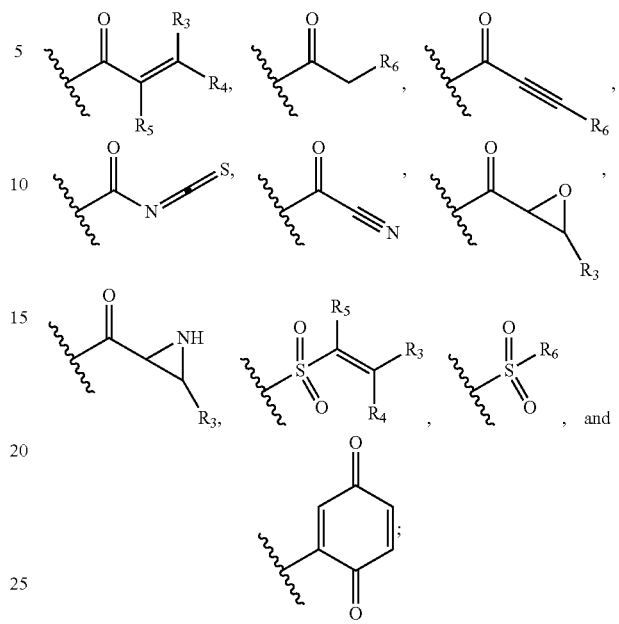

$R_1$ and $R_2$ are independently selected from the group consisting of hydrogen, halogen, $C_{1-6}$ alkyl, $C_{1-6}$ alkoxy, and $C_{1-6}$ haloalkyl;

$R_3$ and $R_4$ are independently selected from the group consisting of hydrogen, $C_{1-6}$ alkyl, $C_{1-6}$ haloalkyl, $C_{1-6}$ heteroalkyl, $C_{1-6}$ haloheteroalkyl, $C_{3-6}$ cycloalkyl, $C_{3-6}$ halocycloalkyl, $C_{2-6}$ heterocycloalkyl, $C_{2-6}$ haloheterocycloalkyl, cyano and ester groups;

$R_5$ is hydrogen;

$R_6$ is selected from the group consisting of hydrogen, halogen, diazo and $C_{1-6}$ alkyl (e.g. methyl).

In one embodiment, Ar is preferably a substituted or unsubstituted heteroaryl, more preferably a five-membered heteroaryl, especially a nitrogen-substituted five-membered heteroaryl such as pyrazolyl and pyrrolyl, and the like.

In one embodiment, $R_1$ is preferably hydrogen, halogen, $C_{1-4}$ alkyl (e.g. methyl, ethyl, propyl and butyl, especially methyl), $C_{1-4}$ alkoxy (e.g. methoxy, ethoxy, propoxy and butoxy, especially methoxy), or $C_{1-4}$ haloalkyl (e.g. halomethyl, haloethyl, halopropyl and halobutyl, especially halomethyl, such as difluoromethyl, trifluoromethyl, chloromethyl, dichloromethyl, and the like).

In one embodiment, $R_2$ is hydrogen.

In one embodiment, $R_3$ and $R_4$ are preferably independently selected from the group consisting of hydrogen, cyano, ester, $C_{1-4}$ haloalkyl (e.g., halomethyl, haloethyl, halopropyl and halobutyl, especially halomethyl, such as chloromethyl, bromomethyl, and the like), and $C_{1-4}$ heteroalkyl (e.g., N-substituted C1-4 alkyl). In one embodiment, the ester group is preferably a —COOR group wherein R is $C_{1-6}$ alkyl, and R is preferably $C_{1-4}$ alkyl such as methyl, ethyl, propyl and butyl.

In one embodiment, $R_6$ is preferably hydrogen, halogen, diazo or methyl.

In one aspect, the present invention preferably provides compounds selected from the group consisting of N-(2-methyl-5-(2-oxo-9-(1H-pyrazol-1-yl)benzo[H][1,6]naphthyridin-1(2H)-yl)phenyl)acrylamide, (E)-4-(dimethylamino)-N-(2-methyl-5-(2-oxo-9-(1H-pyrazol-1-yl)benzo

[H][1,6]naphthyridin-1(2H)-yl)phenyl)-2-butenamide, 2-fluoro-N-(2-methyl-5-(2-oxo-9-(1H-pyrazol-1-yl)benzo[H][1,6]naphthyridin-1(2H)-yl)phenyl) acetamide, 2-chloro-N-(2-methyl-5-(2-oxo-9-(1H-pyrazol-1-yl)benzo[H][1,6]naphthyridin-1(2H)-yl)phenyl)acetamide, 2-bromo-N-(2-methyl-5-(2-oxo-9-(1H-pyrazol-1-yl)benzo[H][1,6]naphthyridin-1(2H)-yl)phenyl) acetamide, 2-iodo-N-(2-methyl-5-(2-oxo-9-(1H-pyrazol-1-yl)benzo[H][1,6]naphthyridin-1(2H)-yl)phenyl)acetamide, N-(2-methyl-5-(2-oxo-9-(1H-pyrazol-1-yl)benzo[H][1,6]naphthyridin-1(2H)-yl)phenyl)azoacetamide, (E)-4-chloro-N-(2-methyl-5-(2-oxo-9-(1H-pyrazol-1-yl)benzo[H][1,6]naphthyridin-1(2H)-yl)phenyl)-2-butenamide, (E)-4-bromo-N-(2-methyl-5-(2-oxo-9-(1H-pyrazol-1-yl)benzo[H][1,6]naphthyridin-1(2H)-yl)phenyl)-2-butenamide, N-(2-methyl-5-(2-oxo-9-(1H-pyrazol-1-yl)benzo[H][1,6]naphthyridin-1(2H)-yl)phenyl)propynamide, (2-methyl-5-(2-oxo-9-(1H-pyrazol-1-yl)benzo[H][1,6]naphthyridin-1(2H)-yl)phenyl) carbamoyl isothiocyanate, cyano-N-(2-methyl-5-(2-oxo-9-(1H-pyrazol-1-yl)benzo[H][1,6]naphthyridin-1(2H)-yl)phenyl)formamide, N-(2-methyl-5-(2-oxo-9-(1H-pyrazol-1-yl)benzo[H][1,6]naphthyridin-1(2H)-yl)phenyl)oxirane-2-carboxamide, N-(2-methyl-5-(2-oxo-9-(1H-pyrazol-1-yl)benzo[H][1,6]naphthyridin-1(2H)-yl)phenyl)azetidine-2-carboxamide, N-(2-methyl-5-(2-oxo-9-(1H-pyrazol-1-yl)benzo[H][1,6]naphthyridin-1(2H)-yl)phenyl)ethenesulfonamide, 2-methyl-5-(2-oxo-9-(1H-pyrazol-1-yl)benzo[H][1,6]naphthyridin-1(2H)-yl)phenylsulfamoyl fluoride, ethyl (E)-2-cyano-3-(N-(2-methyl-5-(2-oxo-9-(1H-pyrazol-1-yl)benzo[H][1,6]naphthyridin-1(2H)-yl)phenyl)sulfamoyl)acrylate, 2-(2-methyl-5-(2-oxo-9-(1H-pyrazol-1-yl) benzo[H][1,6]naphthyridin-1(2H)-yl)phenylamino)benzoquinone, N-(2-methyl-5-(2-oxo-9-(1H-pyrazol-1-yl)benzo[H][1,6]naphthyridin-1(2H)-yl) phenyl) propionamide, N-(2-(difluoromethyl)-5-(2-oxo-9-(1H-pyrazol-1-yl) benzo[H][1,6]naphthyridin-1(2H)-yl)phenyl)acrylamide, N-(2-fluoro-5-(2-oxo-9-(1H-pyrazol-1-yl)benzo[H][1,6]naphthyridin-1(2H)-yl)phenyl) acrylamide, N-(2-chloro-5-(2-oxo-9-(1H-pyrazol-1-yl)benzo[H][1,6]naphthyridin-1(2H)-yl)phenyl)acrylamide, N-(2-bromo-5-(2-oxo-9-(1H-pyrazol-1-yl)benzo[H][1,6]naphthyridin-1(2H)-yl)phenyl)acrylamide, N-(2-iodo-5-(2-oxo-9-(1H-pyrazol-1-yl)benzo[H][1,6]naphthyridin-1(2H)-yl)phenyl) acrylamide, N-(5-(2-oxo-9-(1H-pyrazol-1-yl)benzo[H][1,6]naphthyridin-1(2H)-yl)phenyl)acrylamide, N-(2-trifluoromethyl-5-(2-oxo-9-(1H-pyrazol-1-yl)benzo[H][1,6]naphthyridin-1(2H)-yl)phenyl) acrylamide, N-(2-dichloromethyl-5-(2-oxo-9-(1H-pyrazol-1-yl)benzo[H][1,6]naphthyridin-1(2H)-yl)phenyl)acrylamide, N-(2-chloromethyl-5-(2-oxo-9-(1H-pyrazol-1-yl)benzo[H][1,6]naphthyridin-1(2H)-yl)phenyl) acrylamide, N-(2-methoxy-5-(2-oxo-9-(1H-pyrazol-1-yl)benzo[H][1,6]naphthyridin-1(2H)-yl)phenyl)acrylamide, and N-(2-methyl-5-(2-oxo-9-(1H-pyrrol-1-yl)benzo[H][1,6]naphthyridin-1(2H)-yl)phenyl)acrylamide.

Structures of the preferable compounds are shown below:

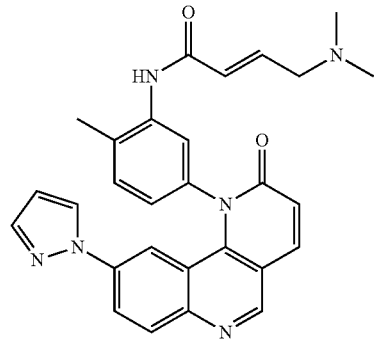

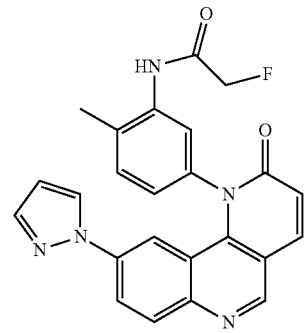

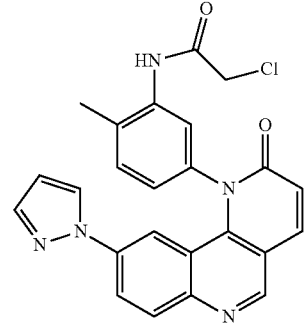

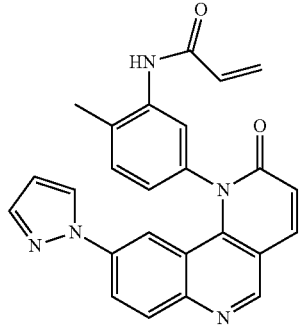

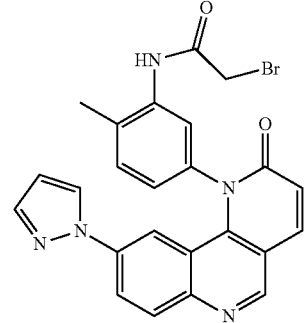

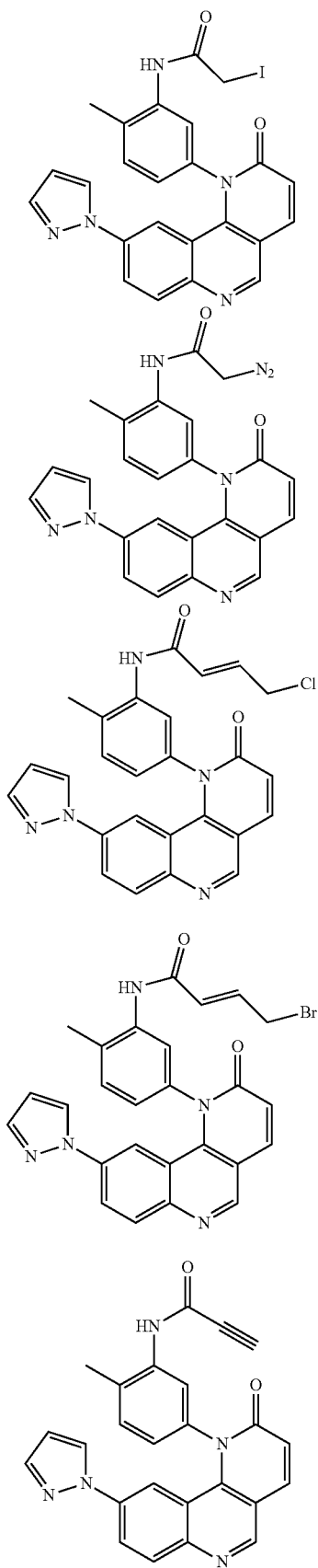
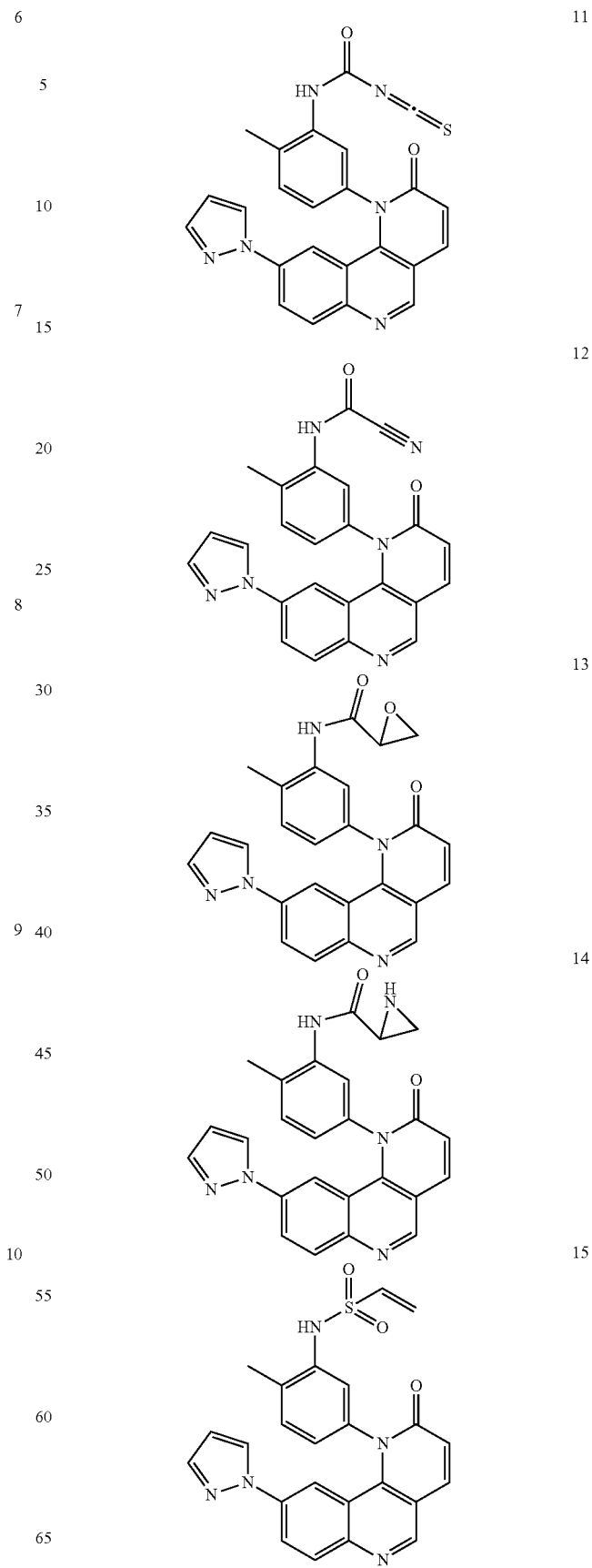

| 16 | 20 |
|---|---|
| 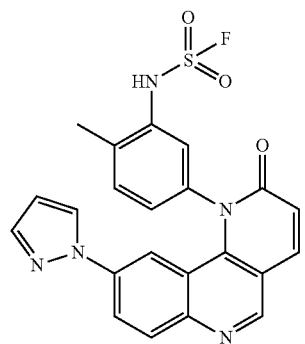 | 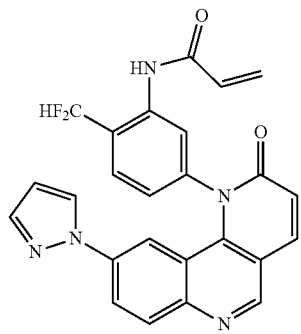 |
| 17 | 21 |
| 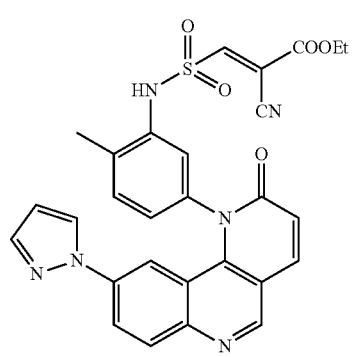 | 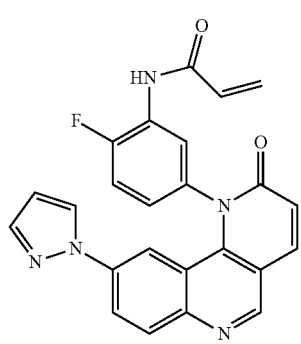 |
| 18 | 22 |
| 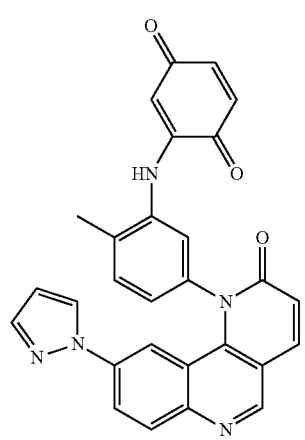 | 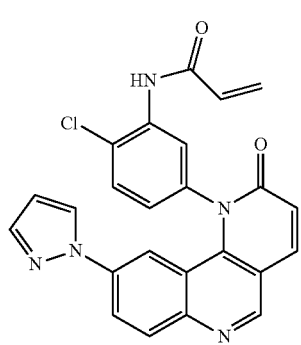 |
| 19 | 23 |
| 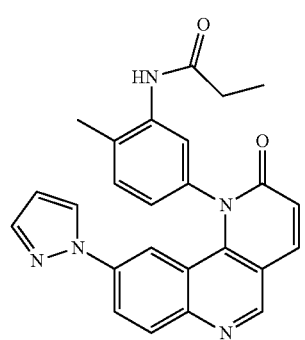 | 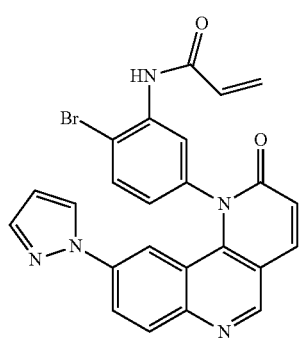 |

24

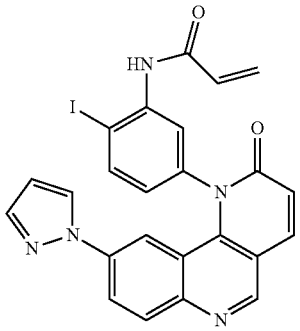

25

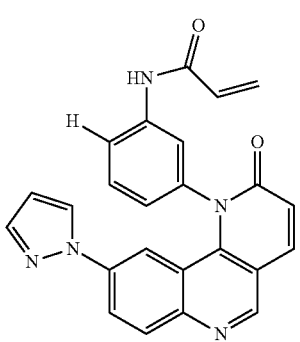

26

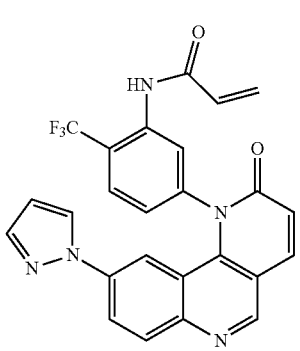

27

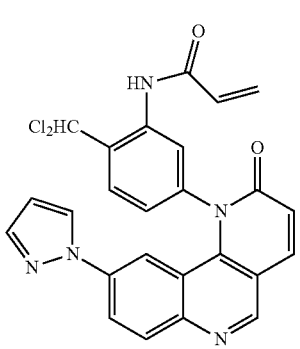

28

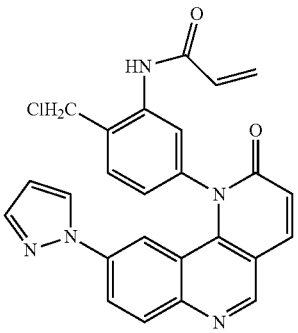

29

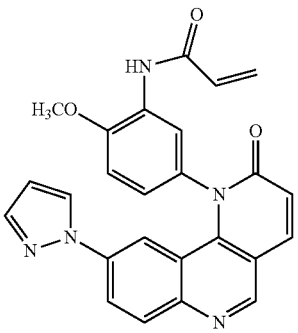

30

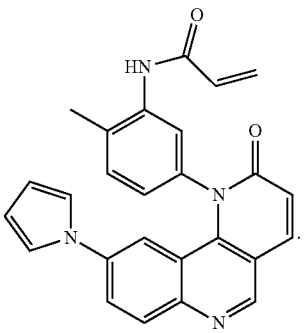

In another aspect, the present application provides a pharmaceutical composition comprising a therapeutically effective amount of at least one compound provided herein, or a pharmaceutically acceptable salt, solvate, ester, acid, metabolite or prodrug thereof, and a pharmaceutically acceptable carrier or excipient, and optionally other therapeutic agents.

The present application provides a method for formulating a pharmaceutical composition for administration by appropriate routes and means comprising an effective concentration of one or more compounds provided herein, or pharmaceutically acceptable salts, solvates, esters, acids, metabolites or prodrugs thereof, that deliver amounts effective for the treatment, prevention or amelioration of one or more symptoms of diseases, disorders or conditions that are modulated or otherwise affected by tyrosine kinase activity, or in which tyrosine kinase activity is implicated. The effective amounts and concentrations are effective for ameliorating the symptoms of any of the diseases, disorders or conditions disclosed herein.

In one aspect, provided herein are methods for treating a patient by administering a compound or a pharmaceutical composition provided herein. In some embodiments, provided herein is a method for inhibiting the activity of Bruton's tyrosine kinase(s), or for treating a disease, disorder, or condition, which would benefit from the inhibition of Bruton's tyrosine kinase(s), which includes administering to the patient a therapeutically effective amount of at least one of any of the compounds herein, or pharmaceutically acceptable salts, solvates, esters, acids, metabolites or prodrugs thereof, or pharmaceutical compositions.

In a further aspect, the above diseases, disorders or conditions that are modulated or otherwise affected by tyrosine kinase activity, or in which tyrosine kinase activity is implicated, include cancer, such as initiation or progression of solid tumor, B-cell lymphoma, sarcoma, lymphoma, diffuse large B-cell lymphoma, follicular lymphoma, chronic lymphocytic lymphoma, acute myeloid leukemia (AML), chronic lymphocytic leukemia (CLL), acute lymphocytic leukemia (ALL), acute promyelocytic leukemia (APL), chronic myeloid leukemia (CML), B-cell prolymphocytic leukemia, lymphoplasmacytic lymphoma/Waldenström macroglobulinemia, splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma/leukemia, lymphomatoid granulomatosis, breast ductal carcinoma, lobular carcinoma, adenocarcinoma, small cell lung cancer, non-small cell lung cancer, melanoma, B-cell proliferative disease, or the like, and the combination thereof. In one embodiment, the present invention is particularly preferred for the treatment of acute myeloid leukemia (AML), chronic lymphocytic leukemia (CLL), acute lymphocytic leukemia (ALL), acute promyelocytic leukemia (APL), chronic myeloid leukemia (CML), B-cell proliferative disease, such as chronic lymphocytic lymphoma, diffuse large B-cell lymphoma (DLBCL), follicular lymphoma or chronic lymphocytic leukemia, or the like, and the combination thereof.

In some embodiments, the invention relates to the treatment of the subject in need who is suffering from an autoimmune disease, e.g., arthritis, rheumatic arthritis, osteoarthritis, lupus, rheumatoid arthritis, inflammatory bowel disease, psoriatic arthritis, osteoarthritis, Still's disease, juvenile arthritis, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myoclonus syndrome, ankylosing spondylosis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

Another aspect of the present application relates to an inhibited tyrosine kinase, including Bruton's tyrosine kinases, Bruton's tyrosine kinase homologs or Btk tyrosine kinase cysteine homologs thereof, which are covalently bound with the inhibitor of the invention. In a further embodiment, the inhibitor is covalently bound to the cysteine residue of a tyrosine kinase.

In a further aspect, the invention provides a method for treating diseases, disorders or conditions that are modulated or otherwise affected by tyrosine kinase activity, or in which tyrosine kinase activity is implicated (such as cancer), by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase or Bruton's tyrosine kinase homolog.

In one embodiment, the compound selectively and irreversibly binds to BTK. In another embodiment, the compound selectively and irreversibly binds to tyrosine kinase JAK3 (Janus Kinase 3). In another embodiment, the compound selectively and irreversibly binds to bone marrow tyrosine kinase in chromosome X (bone marrow X kinase, BMX). In another embodiment, the compound selectively and irreversibly binds to epidermal growth factor receptor (EGFR).

In another aspect, the invention relates to methods for modulating, including irreversibly inhibiting the activity of Btk or other tyrosine kinases, wherein the other tyrosine kinases share homology with Btk by having a cysteine residue (including a Cys 481 residue) that can form a covalent bond with at least one irreversible inhibitor described herein, in a mammal comprising administering to the mammal at least once an effective amount of a compound of formula (I), or a pharmaceutically acceptable salt, solvate, ester, acid, metabolite or prodrug thereof, or a pharmaceutical composition comprising the compound of formula (I).

In another aspect, the application relates to the use of a compound of formula (I) or a pharmaceutically acceptable salt, solvate, ester, acid, metabolite or prodrug thereof in the manufacture of a medicament for the treatment of the above mentioned diseases, disorders or conditions. The application also relates to the use of a compound of formula (I), or a pharmaceutically acceptable salt, solvate, ester, acid, metabolite or prodrug thereof in the manufacture of a medicament for modulating, including irreversibly inhibiting Btk or other tyrosine kinase activity in a mammal.

In further or alternative embodiments, the compound of formula (I), or a pharmaceutically acceptable salt, solvate, ester, acid, metabolite or prodrug thereof is an irreversible inhibitor of Bruton's tyrosine kinase (Btk). In still further or alternative embodiments, such irreversible inhibitors are selective for Btk. In even further or alternative embodiments, such inhibitors have an $EC_{50}$ below 10 µM in enzyme assay. In one embodiment, a Btk irreversible inhibitor has an EC50 of less than 1 µM, and in another embodiment, less than 0.3 µM.

In further or alternative embodiments, the compounds of formula (I) are selective irreversible inhibitors for Btk over Itk (Interleukin 2 (IL-2) inducible T-cell kinase). In further or alternative embodiments, the compounds of formula (I) are selective irreversible inhibitors for Btk over Lck (lymphocyte-specific protein tyrosine kinase). In further or alternative embodiments, the compounds of formula (I) are selective irreversible inhibitors for Btk over ABL (Abelson tyrosine-protein kinase 1, Abelson nonreceptor tyrosine kinase). In further or alternative embodiments, the compounds of formula (I) are selective irreversible inhibitors for Btk over CMET (Hepatocyte growth factor receptor, HGFR, Hepatocyte growth factor receptor). In further or alternative embodiments, the compounds of formula (I) are selective irreversible inhibitors for Btk over EGFR. In further or alternative embodiments, the compounds of formula (I) are selective irreversible inhibitors for Btk over Lyn (V-yes-1 Yamaguchi sarcoma viral related oncogene homolog, Lyn kinase).

In further or alternative embodiments, the irreversible Btk inhibitors are also inhibitors of JAK3.

In further or alternative embodiments, the irreversible Btk inhibitors are also inhibitors of EGFR.

In further or alternative embodiments, the irreversible Btk inhibitors are also inhibitors of BMX.

Other objects, features and advantages of the compounds, compositions, methods and uses described herein will become apparent from the following detailed description. It should be understood that specific embodiments are given by way of illustration only, and various changes and modifications within the spirit and scope of the present disclosure will become apparent to those skilled in the art from this detailed description. All documents, or portions of documents, cited in the application including, but not limited to, patents, patent applications, articles, books, manuals, and treatises are hereby expressly incorporated by reference in their entirety for any purpose.

DETAILED DESCRIPTION OF THE INVENTION

Terminology

Figure 1:
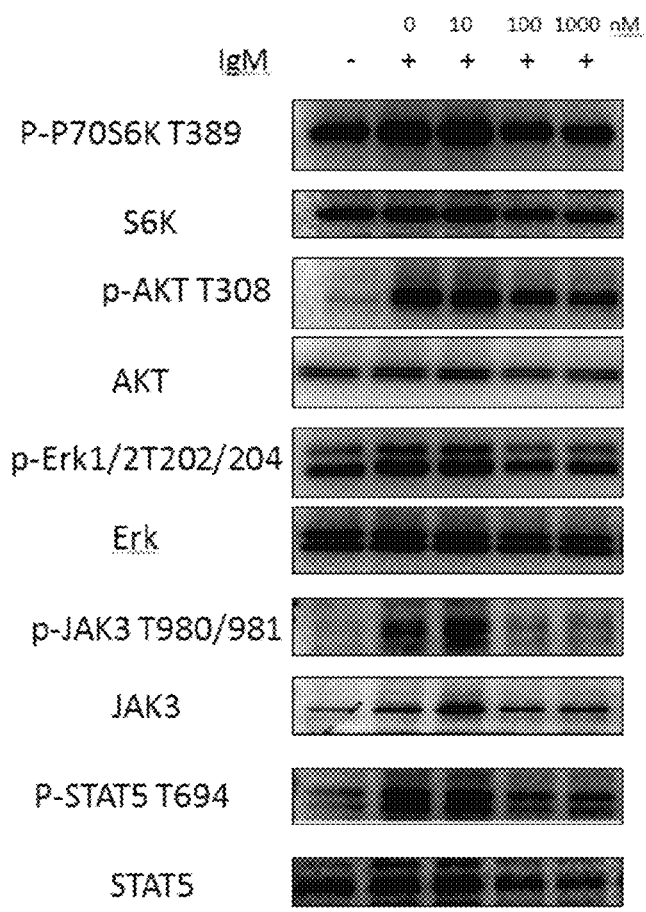
FIG. 1 illustrates the effect of Compound 1 on signaling pathways in Ramos cells.
Figure 1:
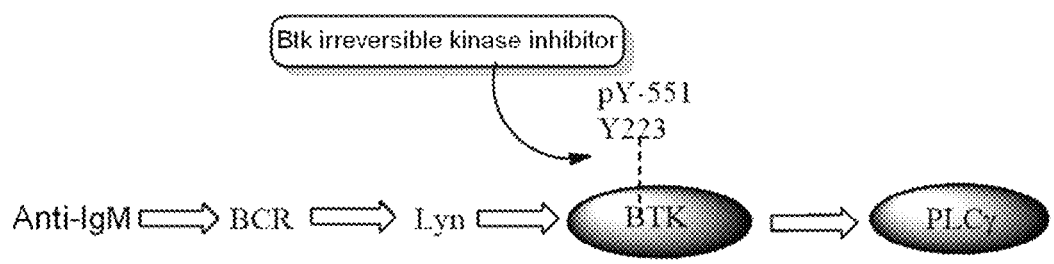

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferable a "lower alkyl" having 1 to 6 carbon atoms. Typical alkyl groups include, but are not limited to, methyl, ethyl, propyl, isopropyl, butyl, isobutyl, tertiary butyl, pentyl, hexyl, and the like.

"Alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

"Alkoxyalkyl" refers to an alkyl radical, as defined herein, substituted with an alkoxy group, as defined herein.

The term "alkylamine" refers to a —N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed from five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

"Alkyl(aryl)" means an alkyl radical, as defined herein, substituted with an aryl group, as defined herein. Non-limiting alkyl(aryl) groups include benzyl, phenethyl, and the like.

The term "cycloalkyl" refers to a monocyclic or polycyclic radical that contains only carbon and hydrogen. Cycloalkyl groups include groups having from 3 to 10 ring atoms. Depending on the structure, a cycloalkyl group can be a monoradical or a diradical (e.g., an cycloalkylene group). In the invention, the cycloalkyl group is preferably a cycloalkyl having 3 to 8 carbon atoms, and more preferably a "lower cycloalkyl" having 3 to 6 carbon atoms.

"Alkyl(cycloalkyl)" means an alkyl radical, as defined herein, substituted with a cycloalkyl group, as defined herein. Non-limiting alkyl(cycloalkyl) groups include cyclopropylmethyl, cyclobutylmethyl, cyclopentylmethyl, cyclohexylmethyl, and the like.

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

As used herein, the term "heterocycloalkyl" refers to a non-aromatic ring wherein one or more atoms forming the ring is a heteroatom selected from nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heteroaryl)" means an alkyl radical, as defined herein, substituted with a heteroaryl group, as defined herein.

The term "alkyl(heterocycloalkyl)" means an alkyl radical, as defined herein, substituted with a heterocycloalkyl group, as defined herein.

The term "halo" or "halogen" means fluoro, chloro, bromo and iodo.

The terms "haloalkyl", "haloalkoxy" and "haloheteroalkyl" include alkyl, alkoxy and heteroalkyl structures in which at least one hydrogen is replaced with a halogen atom. In certain embodiments in which two or more hydrogen atoms are replaced with halogen atoms, the halogen atoms are the same or different as one another.

As used herein, the term "cyano" refers to —CN group.

The term "ester" refers to a chemical moiety with formula —COOR, where R is selected from among alkyl, cycloalkyl, aryl, heteroaryl (bonded through a ring carbon) and heteroalicyclic (bonded through a ring carbon).

The term "optionally substituted" or "substituted" means that the referenced group may be substituted with one or more additional group(s) individually and independently selected from alkyl, cycloalkyl, aryl, heteroaryl, hydroxy, alkoxy, cyano, halo, amide, nitro, haloalkyl, amino, and the like.

The term "Bruton's tyrosine kinase" as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog" as used herein, refers to orthologs of Bruton's tyrosine kinase, e.g., the orthologs from mouse (GenBank Acession No. AAB47246), dog (GenBank Acession No. XP_549139.), rat (GenBank Acession No. NP_001007799), chicken (GenBank Acession No. NP_989564), or zebra fish (GenBank Acession No. XP_698117), and fusion proteins of any of the foregoing that exhibit kinase activity towards one or more substrates of Bruton's tyrosine kinase (e.g. a peptide substrate having the amino acid sequence AVLESEEELYSSARQ).

The term "homologous cysteine" as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. Other examples of kinases having homologous cysteines are shown in Table 1. See also the sequence alignments of tyrosine kinases (TK) published on the World Wide Web at kmase.com/human/kinome/phylogeny.html.

TABLE 1

A sequence comparison of Btk with other tyrosine kinases.

| # | 473 | <u>474</u> | 475 | 476 | 477 | 478 | 479 | 480 | <u>481</u> | 482 | 483 |
|---|-----|-----|-----|-----|-----|-----|-----|-----|-----|-----|-----|
| BTK | I | <u>T</u> | E | Y | M | A | N | G | <u>C</u> | L | L |
| BMX | V | <u>T</u> | E | Y | M | A | R | G | <u>C</u> | L | L |
| TEC | V | <u>T</u> | E | F | M | E | R | G | <u>C</u> | L | L |
| TXK | V | <u>T</u> | E | F | M | E | N | G | <u>C</u> | L | L |
| ITK | V | <u>F</u> | E | F | M | E | H | G | <u>C</u> | L | S |
| EGFR | I | <u>T</u> | Q | L | M | P | F | G | <u>C</u> | L | L |
| ErbB2 | V | <u>T</u> | Q | L | M | P | Y | G | <u>C</u> | L | L |
| ErbB4 | V | <u>T</u> | Q | L | M | P | H | G | <u>C</u> | L | L |
| JAK3 | V | <u>M</u> | E | Y | L | P | S | G | <u>C</u> | L | R |
| BLK | V | <u>T</u> | E | Y | L | P | S | G | <u>C</u> | L | L |
| LCK | I | <u>T</u> | E | Y | M | E | N | G | <u>S</u> | L | V |
| LYN | I | <u>T</u> | E | Y | M | A | K | G | <u>S</u> | L | L |
| SYK | V | <u>M</u> | E | M | A | E | L | G | <u>P</u> | L | N |

The terms "inhibits", "inhibiting", or "inhibitor" of a kinase, as used herein, refer to inhibition of phosphotransferase activity.

The term "irreversible inhibitor" as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible Btk inhibitor" as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase, as shown in Table 1.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, a target protein is Btk.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

The Inhibitors of Bruton's Tyrosine Kinase of the Invention

The invention provides a compound of formula (I), or a pharmaceutically acceptable salt, solvate, ester, acid, metabolite or prodrug thereof:

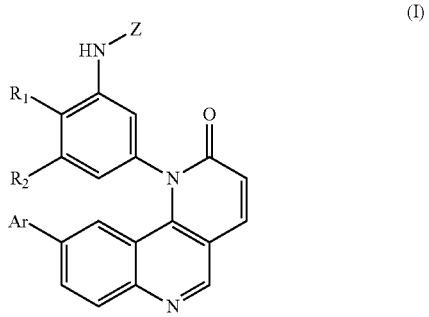

wherein, Ar is selected from the group consisting of aryl and heteroaryl;

Z is selected from the group consisting of

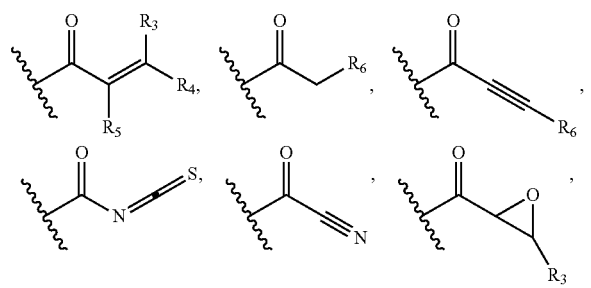

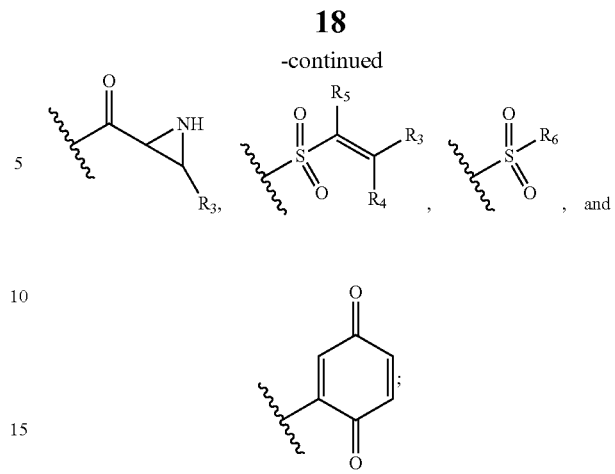

$R_1$ and $R_2$ are independently selected from the group consisting of hydrogen, halogen, $C_{1-6}$ alkyl, $C_{1-6}$ alkoxy, and $C_{1-6}$ haloalkyl;

$R_3$ and $R_4$ are independently selected from the group consisting of hydrogen, $C_{1-6}$ alkyl, $C_{1-6}$ haloalkyl, $C_{1-6}$ heteroalkyl, $C_{1-6}$ haloheteroalkyl, $C_{3-6}$ cycloalkyl, $C_{3-6}$ halocycloalkyl, $C_{2-6}$ heterocycloalkyl, $C_{2-6}$ haloheterocycloalkyl, cyano and ester groups;

$R_5$ is hydrogen;

$R_6$ is selected from the group consisting of hydrogen, halogen, diazo and $C_{1-6}$ alkyl.

In one embodiment, Ar is preferably a substituted or unsubstituted heteroaryl, more preferably a five-membered heteroaryl, especially a nitrogen-substituted five-membered heteroaryl such as pyrazolyl and pyrrolyl, and the like.

In one embodiment, $R_1$ is preferably hydrogen, halogen, $C_{1-4}$ alkyl (e.g. methyl, ethyl, propyl and butyl, especially methyl), $C_{1-4}$ alkoxy (e.g. methoxy, ethoxy, propoxy and butoxy, especially methoxy), or $C_{1-4}$ haloalkyl (e.g. halomethyl, haloethyl, halopropyl and halobutyl, especially halomethyl, such as difluoromethyl, trifluoromethyl, chloromethyl, dichloromethyl, and the like).

In one embodiment, $R_2$ is hydrogen.

In one embodiment, $R_3$ and $R_4$ are preferably independently selected from the group consisting of hydrogen, cyano, ester, $C_{1-4}$ haloalkyl (e.g., halomethyl, haloethyl, halopropyl and halobutyl, especially halomethyl, such as chloromethyl, bromomethyl, and the like), and $C_{1-4}$ heteroalkyl (e.g., N-substituted C1-4 alkyl). In one embodiment, the ester group is preferably a —COOR group wherein R is $C_{1-6}$ alkyl, and R is preferably $C_{1-4}$ alkyl such as methyl, ethyl, propyl and butyl.

In one embodiment, $R_6$ is preferably hydrogen, halogen, diazo or methyl.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further embodiments of the compounds of formula (I) include, but are not limited to, those selected from the following:

-continued
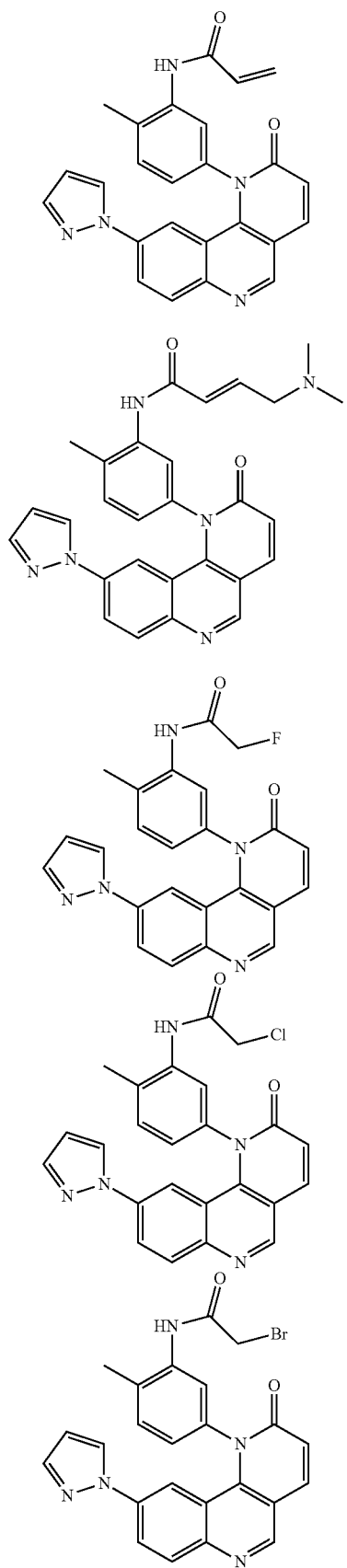
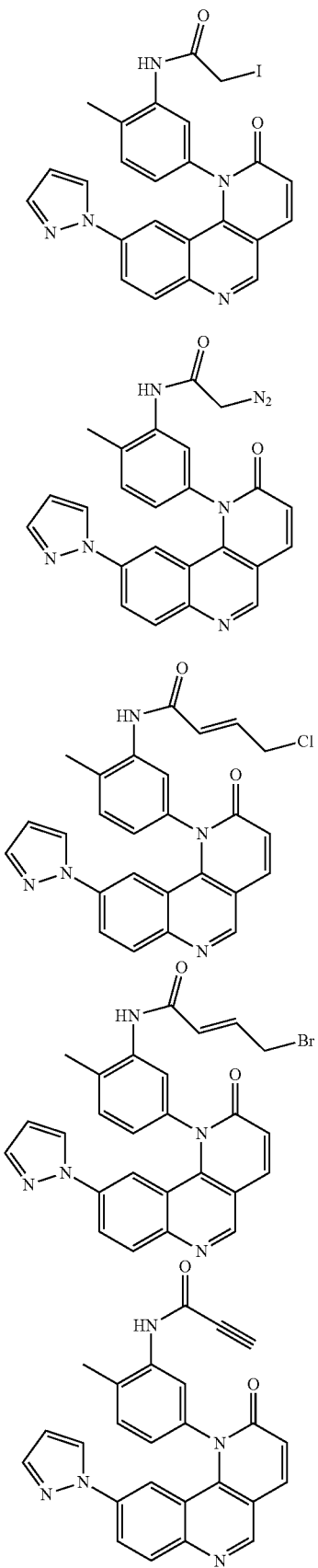

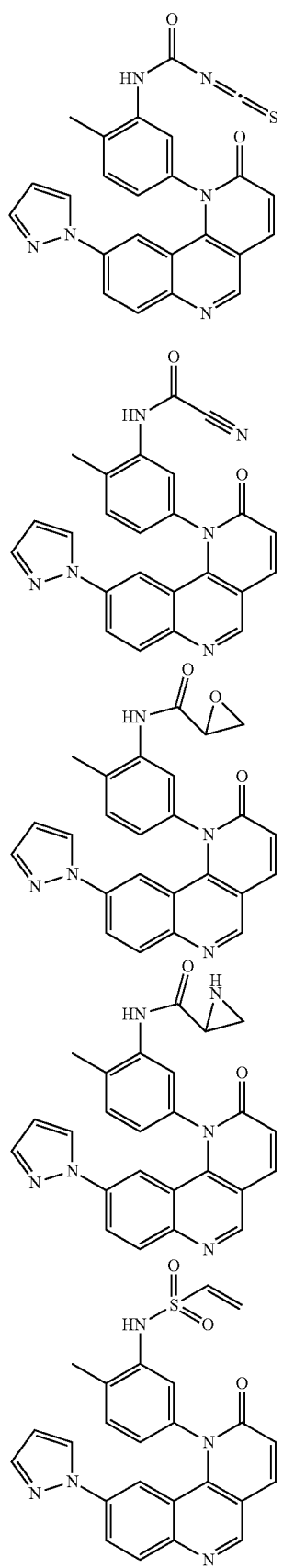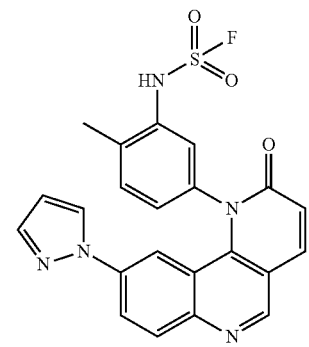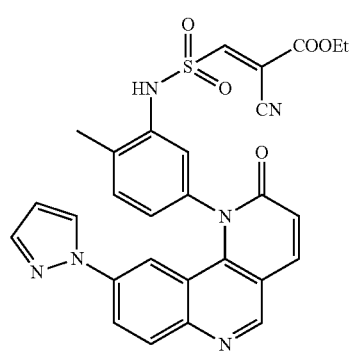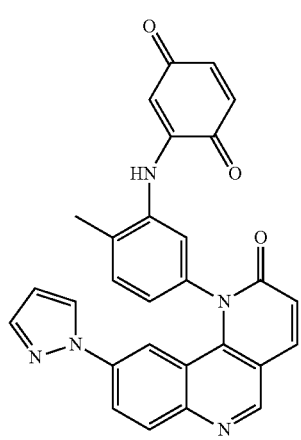

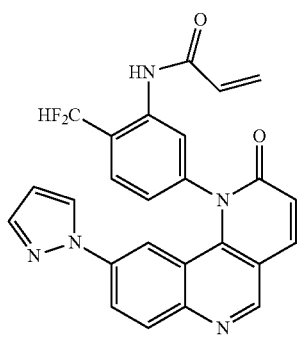
20
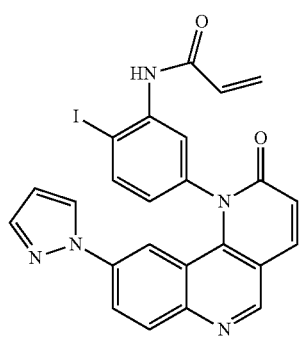
24
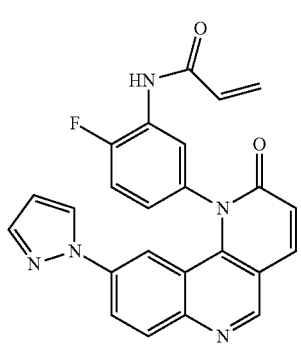
21
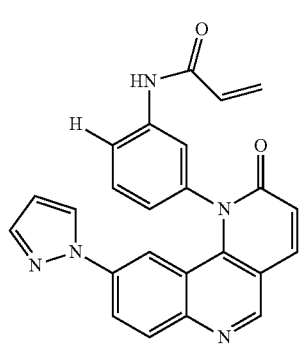
25
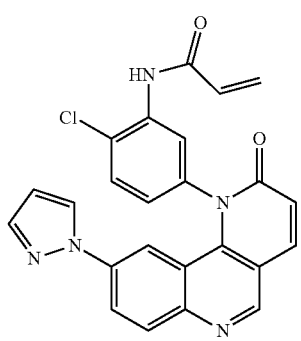
22
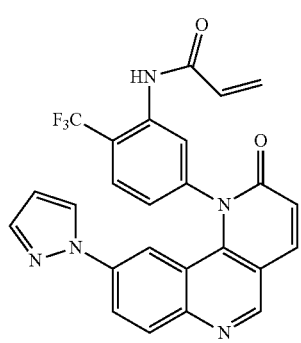
26
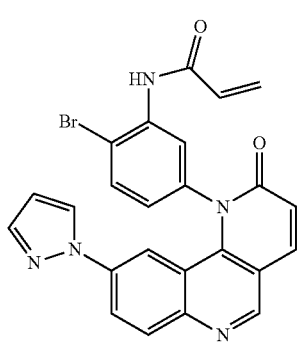
23
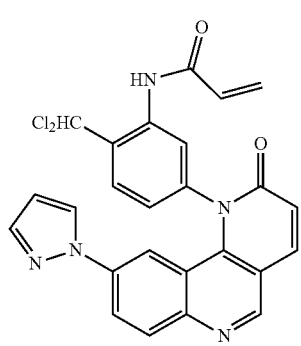
27

-continued
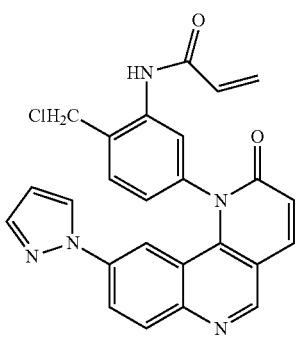
28
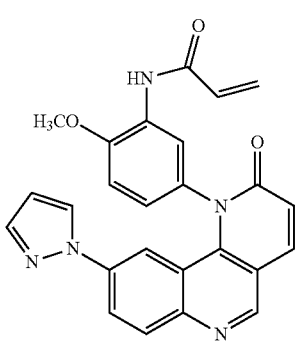
29
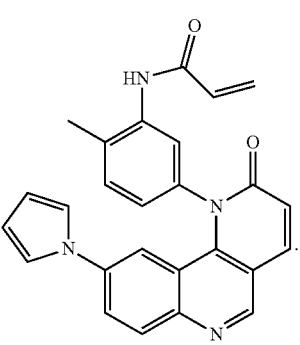
30
In some embodiments, the compounds provided herein as selected from:
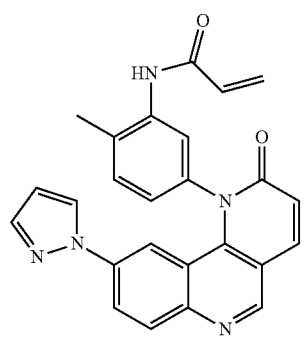
1
-continued
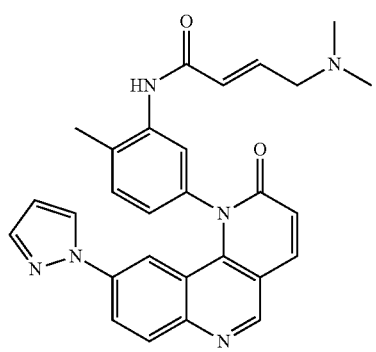
2
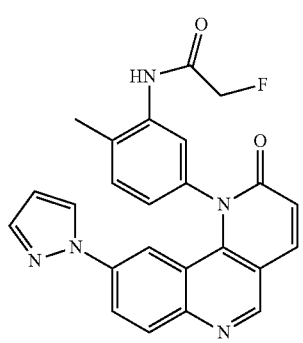
3
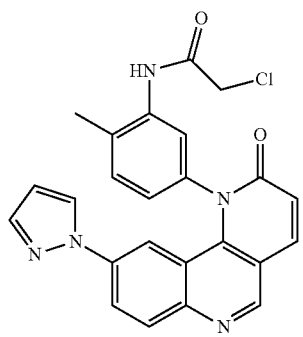
4
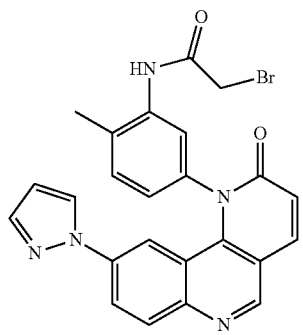
5

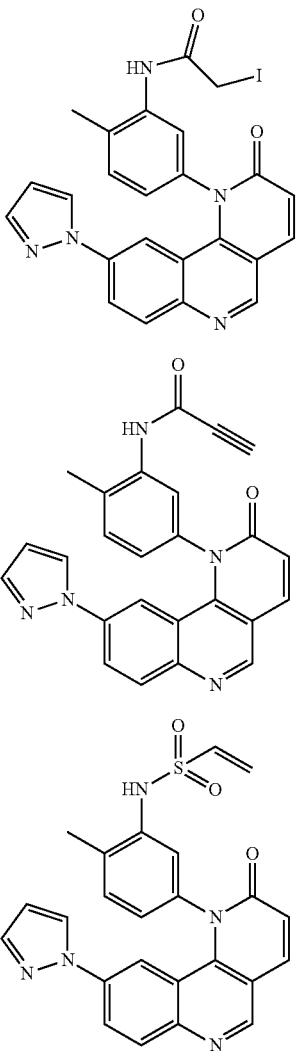

Described herein are compounds that inhibit tyrosine kinases such as Btk activity. The pharmaceutically acceptable salts, solvates, esters, acids, pharmaceutically active metabolites and prodrugs of these compounds are also described herein.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2] oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, and microscopy. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Invention

The application also provides a pharmaceutical composition comprising at least one compound of formula (I), or a pharmaceutically acceptable salt, solvate, ester, acid, pharmaceutically active metabolite or prodrug of the compound, and a pharmaceutically acceptable carrier or excipient, and optionally other therapeutic agents.

In the course of treatment, it may be used alone or in combination with one or more other therapeutic agents. The medicament comprising a compound of the invention may be administered to a patient through at least one of injection, oral, inhalation, rectal and transdermal administration. Other therapeutic agents may be selected from the following: immunosuppressants (e.g., tacrolimus, cyclosporin, rapamycin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (e.g., mTOR inhibitors, c-Met inhibitors) or her2 antibodies. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™ (Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be cytokines such as G-CSF (Granulocyte-Colony Stimulating Factor). Alternatively, other therapeutic agents may be for example, but are not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In the embodiments of the invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

The compound of formula (I) can irreversibly inhibit Btk and can be used in the treatment of patients suffering from conditions or diseases that are involved in or mediated by Bruton's tyrosine kinase, including but not limited to, cancers, autoimmune diseases and other inflammatory diseases. The conditions or diseases are selected from initiation or progression of solid tumor, B-cell lymphoma, sarcoma, lymphoma, diffuse large B-cell lymphoma, follicular lymphoma, chronic lymphocytic lymphoma, acute myeloid leukemia (AML), chronic lymphocytic leukemia (CLL), acute lymphocytic leukemia (ALL), acute promyelocytic leukemia (APL), chronic myeloid leukemia (CML), B-cell prolymphocytic leukemia, lymphoplasmacytic lymphoma/Waldenström macroglobulinemia, splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma/leukemia, lymphomatoid granulomatosis, breast ductal carcinoma, lobular carcinoma, adenocarcinoma, small cell lung cancer, non-small cell lung cancer, melanoma, B-cell proliferative disease, or the like, and the combination thereof. It is particularly preferred for the treatment of acute myeloid leukemia (AML), chronic lymphocytic leukemia (CLL), acute lymphocytic leukemia (ALL), acute promyelocytic leukemia (APL), chronic myeloid leukemia (CML), B-cell proliferative disease, such as chronic lymphocytic lymphoma, diffuse large B-cell lymphoma (DLBCL), follicular lymphoma or chronic lymphocytic leukemia, or the like and the combination thereof.

Preparation of the Compounds

Compounds of formula (I) may be synthesized using standard synthetic techniques known to those of skill in the art or using methods known in the art in combination with methods described herein. In additions, solvents, temperatures and other reaction conditions presented herein may vary according to those of skill in the art. As a further guide the following synthetic methods may also be utilized.

The reactions can be employed in a linear sequence to provide the compounds described herein or they may be used to synthesize fragments which are subsequently joined by the methods described herein and/or known in the art.

The compounds described herein can be modified using various electrophiles or nucleophiles to form new functional groups or substituents. Table 2 lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 2

Examples of Covalent Linkages and Precursors Thereof

| Covalent LinkageProduct | Electrophile | Nucleophile |
|---|---|---|
| carboxamides | activated esters | amines/anilines |
| carboxamides | acyl azides | amines/anilines |
| carboxamides | acyl halides | amines/anilines |
| esters | acyl halides | alcohols/phenols |
| esters | acyl nitriles | alcohols/phenols |
| carboxamides | acyl nitriles | amines/anilines |
| imines | aldehydes | amines/anilines |
| hydrazones | aldehydes or ketones | hydrazines |
| oximes | aldehydes or ketones | hydroxylamines |
| alkyl amines | alkyl halides | amines/anilines |
| esters | alkyl halides | carboxylic acids |
| thioethers | alkyl halides | thiols |
| esters | alkyl halides | alcohols/phenols |
| thioethers | alkyl sulfonates | thiols |
| esters | alkyl sulfonates | carboxylic acids |
| ethers | alkyl sulfonates | alcohols/phenols |
| esters | anhydrides | alcohols/phenols |
| carboxamides | anhydrides | amines/anilines |
| thiophenols | aryl halides | thiols |
| aryl amines | aryl halides | amines |
| thioethers | azindine | thiols |
| boronate esters | boronates | glycols |
| carboxamides | carboxylic acids | amines/anilines |
| esters | carboxylic acids | alcohols |
| hydrazines | hydrazides | carboxylic acids |
| N-acylureas or anhydrides | carbodiimides | carboxylic acids |
| esters | diazoalkanes | carboxylic acids |
| thioethers | epoxids | thiols |
| thioethers | haloacetamides | thiols |
| ammotriazines | halotriazines | amines/anilines |
| triazinyl ethers | halotriazines | alcohols/phenols |
| amidines | imido esters | amines/anilines |
| ureas | isocyanates | amines/anilines |
| urethanes | isocyanates | alcohols/phenols |
| thioureas | isothiocyanates | amines/anilines |
| thioethers | maleimides | thiols |
| phosphite esters | phosphoramidites | alcohols |
| silyl ethers | silyl halides | alcohols |
| alkyl amines | sulfonate esters | amines/anilines |
| thioethers | sulfonate esters | thiols |
| esters | sulfonate esters | carboxylic acids |
| ethers | sulfonate esters | alcohols |
| sulfonamides | sulfonyl halides | amines/anilines |

TABLE 2-continued

Examples of Covalent Linkages and Precursors Thereof

| Covalent LinkageProduct | Electrophile | Nucleophile |
|---|---|---|
| sulfonate esters | sulfonyl halides | phenols/alcohols |
| alkyl thiols | α,β-unsaturated esters | thiols |
| alkyl ethers | α,β-unsaturated esters | alcohols |
| alkyl amines | α,β-unsaturated esters | amines |
| alkyl thiols | vinyl sulfones | thiols |
| alkyl ethers | vinyl sulfones | alcohols |
| alkyl amines | vinyl sulfones | amines |
| vinyl sulfides | propargyl amides | thiols |

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

The starting materials used for the synthesis of the compounds described herein may be synthesized or can be obtained from commercial sources. The compounds described herein, and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

A non-limiting example of a synthetic approach towards the preparation of compounds of formula (I) is shown in Scheme I.

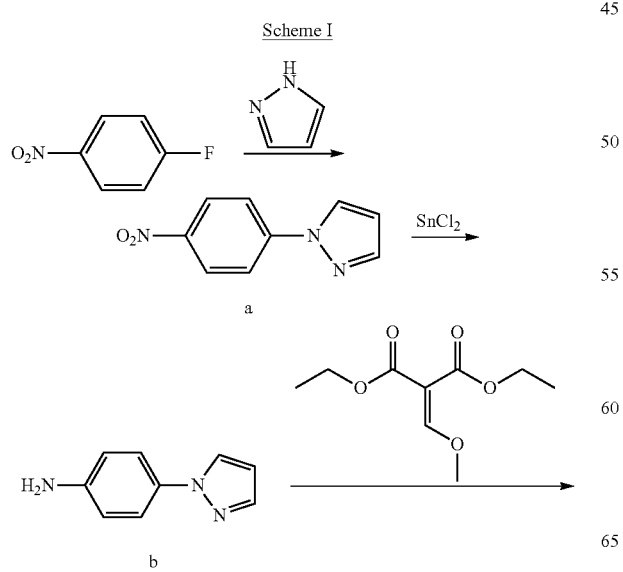

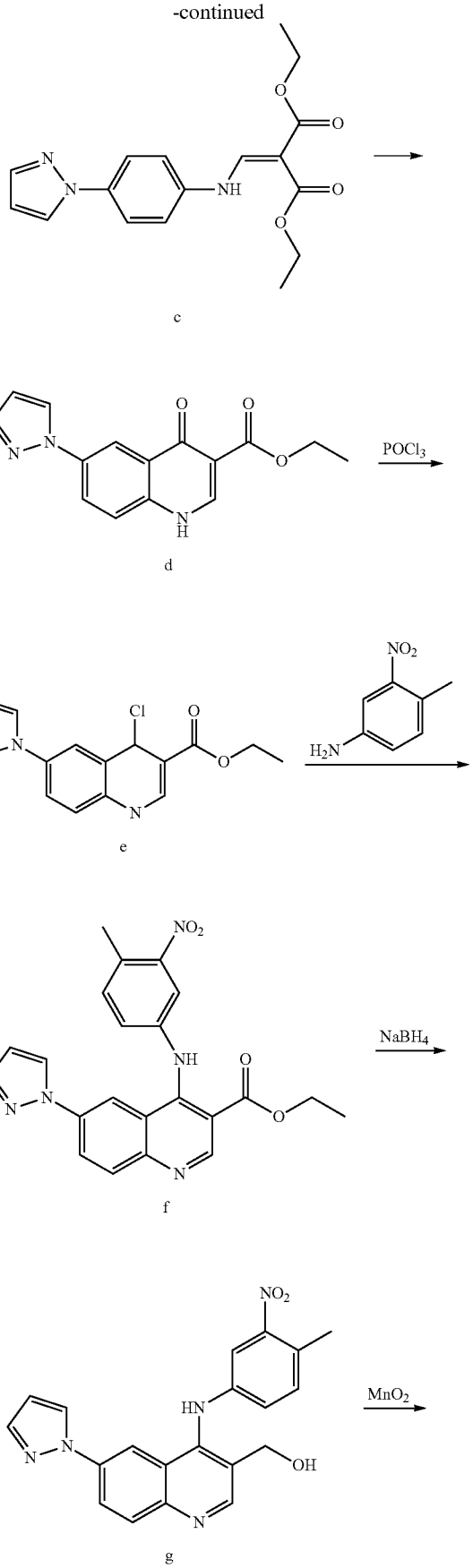

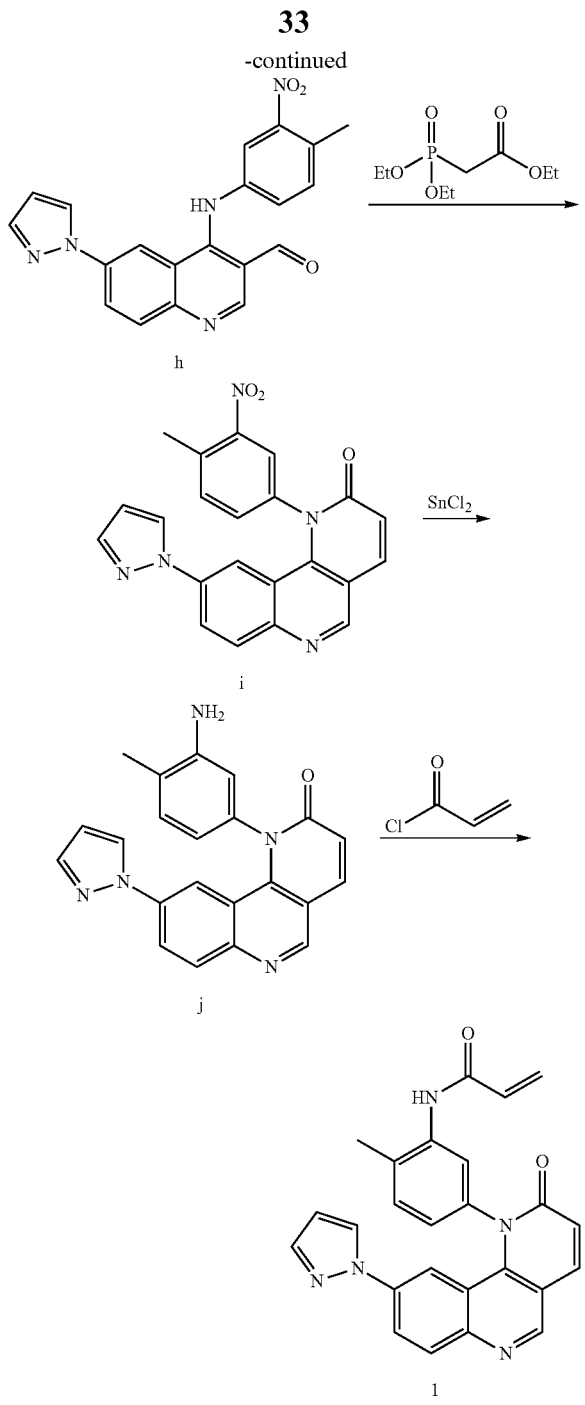

Using the synthetic methods described herein, as well as those known in the art, tyrosine kinase inhibitors as disclosed herein are obtained in good yields and purity. The compounds prepared by the methods disclosed herein are purified by conventional means known in the art, such as, filtration, recrystallization, chromatography, distillation, and combinations thereof.

Sites on the aromatic ring portion of compounds of formula (I) can be susceptible to various metabolic reactions, therefore incorporation of appropriate substituents on the aromatic ring structures, such as, by way of example only, halogens can reduce, minimize or eliminate this metabolic pathway.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

Example 1: Synthesis of the Inventive Compounds

Synthesis of 1-(4-nitrophenyl)-1H-pyrazole a p-Fluoronitrobenzene (10 mmol) and pyrazole (1.2 eq.) were dissolved in N,N-dimethylformamide (20 mL), and then potassium carbonate (1.5 eq.) was added. The resultant was refluxed for 10 hrs. After completion of the reaction, most of the solvent was removed. The resultant was added into water and extracted with ethyl acetate, dried over anhydrous sodium sulphate, filtered and concentrated. After column chromatography, compound a (1.7 g) was obtained in a yield of 90%. Exact Mass (cal.): 189.0538; MS (ESI) m/e $(M+1)^+$: 190.0620.

Synthesis of 1-(4-aminophenyl)-1H-pyrazole b

Compound a (5 mmol) was dissolved in ethanol (15 mL), then stannous chloride hydrate (10 eq.) was added, refluxed for 2 hrs, and cooled. The pH of the solution was adjusted to weakly basic with saturated sodium bicarbonate solution, and then was extracted with ethyl acetate, dried over anhydrous sodium sulfate, filtered and concentrated to give compound b (0.66 g) in 83% yield. Exact Mass (cal.): 159.0796; MS (ESI) m/e $(M+1)^+$: 160.0879.

Synthesis of diethyl 2-((4-(1H-pyrazol-1-yl)phenylamino)methylene) malonate

Compound b (4 mmol) and diethyl ethoxymethylidenemalonate (1.5 eq.) were dissolved in ethanol (15 mL), refluxed for 12 hrs, cooled, filtered and dried to give compound c (1.2 g) in 90% yield. Exact Mass (cal): 329.1376; MS (ESI) m/e $(M+1)^+$: 330.1460.

Synthesis of ethyl 4-oxo-6-(1H-pyrazol-1-yl)-1,4-dihydroquinoline-3-carboxylate d Compound c (3 mmol) was dissolved in diphenyl ether (30 mL), refluxed for 5 hrs, cooled and concentrated to remove most of the solvent. After column chromatography, compound d (0.25 g) was obtained in 30% yield. Exact Mass (cal.): 283.0957; MS (ESI) m/e $(M+1)^+$: 284.1034.

Synthesis of ethyl 4-chloro-6-(1H-pyrazol-1-yl) quinoline-3-carboxylate e

Compound d (2 mmol) was dissolved in acetonitrile (10 mL), followed by the addition of phosphorus oxychloride (1.5 eq.). The resultant was refluxed for 2 hrs. After completion of the reaction, the solvent and excess phosphorous oxychloride were removed and the residues were poured into water, neutralized with saturated sodium bicarbonate solution, extracted with ethyl acetate, dried over anhydrous sodium sulfate, filtered and concentrated. After column chromatography, compound e (0.42 g) was obtained in 70% yield. Exact Mass (cal.): 301.0618; MS (ESI) m/e $(M+1)^+$: 302.0793.

Synthesis of ethyl 4-(4-methyl-3-nitrophenylamino)-6-(1H-pyrazol-1-yl)quinoline-3-carboxylate f Compound e (1 mmol) and 4-methyl-3-nitroaniline (1.2 eq.) were dissolved in 1,4-dioxane (5 mL), refluxed for 10 hrs, cooled, and removed most of the solvent. The resultant was poured into water, neutralized with 1N aqueous sodium hydroxide, then extracted with ethyl acetate, dried over anhydrous sodium sulfate, filtered and concentrated to give compound f (0.35 g) in 85% yield. Exact Mass (cal.): 417.1437; MS (ESI) m/e (M+1)$^+$: 419.16410.

Synthesis of (4-(4-methyl-3-nitrophenylamino)-6-(1H-pyrazol-1-yl) quinolin-3-yl)methanol g Compound f (0.8 mmol) was dissolved in ethanol (15 mL), then sodium borohydride (10 eq.) was added, stirred at room temperature for 12 hrs, cooled, and then quenched with ammonium chloride solution. Most of the ethanol was removed under reduced pressure, and then extracted with ethyl acetate, dried over anhydrous sodium sulfate, filtered, and concentrated. After column chromatography, compound g (0.18 g) was obtained in 60% yield. Exact Mass: 375.1331; MS (ESI) m/e (M+1)$^+$: 376.1410.

Synthesis of 4-(4-methyl-3-nitrophenylamino)-6-(1H-pyrazol-1-yl) quinoline-3-carbaldehyde h Compound g (0.5 mmol) was dissolved in methylene chloride (5 mL) and then activated manganese dioxide (1.5 eq.) was added. The resultant was stirred at room temperature for 12 hrs, filtered and concentrated to give compound h (0.15 g) in 80% yield. Exact Mass (cal.): 373.1175; MS (ESI) m/e (M+1)$^+$: 374.1253.

Synthesis of 1-(4-methyl-3-nitrophenyl)-9-(1H-pyrazol-1-yl)benzo[h][1,6]naphthyridin-2(1H)-one i To a solution of compound h (0.25 mmol) and triethyl phosphonoacetate (1.2 eq.) in ethanol (5 mL), was added potassium carbonate (1.5 eq.), and then refluxed for 24 hrs. After completion of the reaction, most of the solvent was removed. The resultant was poured into water, extracted with ethyl acetate, dried over anhydrous sodium sulfate, filtered and concentrated. After column chromatography, Compound i (0.05 g) was obtained in 50% yield. Exact Mass (cal.): 397.1175; MS (ESI) m/e (M+1)$^+$: 398.1248.

Synthesis of 1-(4-methyl-3-aminophenyl)-9-(1H-pyrazol-1-yl)benzo[H][1,6]naphthyridin-2(1H)-one j Compound i (0.1 mmol) was dissolved in ethanol (2 mL) and then stannous chloride hydrate (10 eq.) was added, refluxed for 2 hrs, and cooled. The solution was adjusted to weak basic pH with saturated sodium bicarbonate solution, and then was extracted with ethyl acetate, dried over anhydrous sodium sulphate, filtered and concentrated to give compound j (0.024 g) in 65% yield. Exact Mass (cal.): 367.1433; MS (ESI) m/e (M+1)$^+$: 368.1507.

Example 1a

Synthesis of N-(2-methyl-5-(2-oxo-9-(1H-pyrazol-1-yl)benzo[H][1,6]naphthyridin-1(2H)-yl)phenyl) acrylamide 1

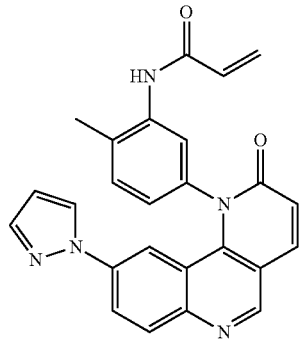 [SMILES: C=CC(=O)Nc1cc(-n2c(=O)ccc3cnc4ccc(-n5cccn5)cc4c32)ccc1C]

Compound j (0.02 mmol) and diisopropylethylamine (1.5 eq.) were dissolved in dichloromethane (0.5 mL) under ice-cooling condition and then acryloyl chloride (1.2 eq.) was added. After reacting for 2 hrs, the reaction was quenched with saturated sodium bicarbonate solution, extracted with dichloromethane, dried over anhydrous sodium sulfate, filtered and concentrated. After column chromatography, Compound 1 (0.006 g) was obtained in 70% yield. Exact Mass (cal.): 421.1539; MS (ESI) m/e (M+1)$^+$: 422.1621; 1H-NMR (400 MHz): 9.79 (s, 1H), 9.14 (s, 1H), 8.32 (d, J=9.6 HZ, 1H), 8.20 (dd, J=8.8, 2.0 HZ, 1H), 8.15 (d, J=9.2 HZ, 1H), 7.71-7.69 (m, 2H), 7.63 (s, 1H), 7.54 (d, J=8.4 HZ, 1H), 7.24 (d, J=7.6 HZ, 1H), 7.13 (s, 1H), 6.95 (d, J=9.2 HZ, 1H), 6.57-6.50 (m, 2H), 6.20 (d, J=17.2 HZ, 1H), 5.76 (d, J=10.8 HZ, 1H), 2.42 (s, 3H).

Example 1b

Synthesis of N-(2-methyl-5-(2-oxo-9-(1H-pyrazol-1-yl)benzo[H][1,6]naphthyridin-1(2H)-yl)phenyl) propynamide 10

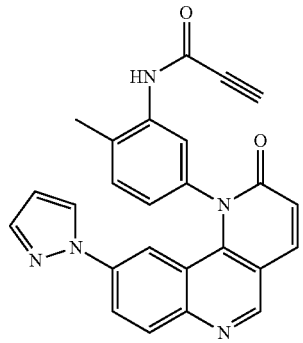 [SMILES: C#CC(=O)Nc1cc(-n2c(=O)ccc3cnc4ccc(-n5cccn5)cc4c32)ccc1C]

The synthesis of Compound 10 was accomplished using a procedure similar to that described in Example 1a. Exact Mass (cal.): 419.1382; MS (ESI) m/e (M+1)$^+$: 420.1371.

Example 1c

Synthesis of 2-fluoro-N-(2-methyl-5-(2-oxo-9-(1H-pyrazol-1-yl)benzo[H][1,6]naphthyridin-1(2H)-yl)phenyl)acetamide 3

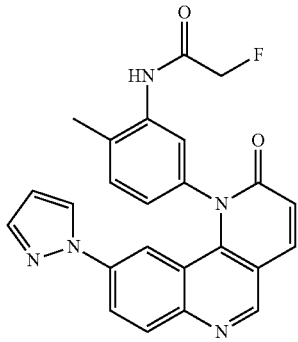 [SMILES: Cc1ccc(-n2c(=O)ccc3cnc4ccc(-n5cccn5)cc4c32)cc1NC(=O)CF]

The synthesis of Compound 3 was accomplished using a procedure similar to that described in Example 1a. Exact Mass (cal.): 427.1445; MS (ESI) m/e (M+1)$^+$: 428.1480.

Example 1d

Synthesis of 2-chloro-N-(2-methyl-5-(2-oxo-9-(1H-pyrazol-1-yl) benzo[H][1,6]naphthyridin-1(2H)-yl)phenyl)acetamide 4

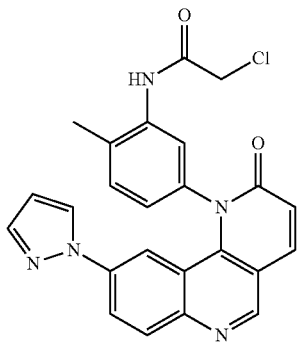 [SMILES: Cc1ccc(-n2c(=O)ccc3cnc4ccc(-n5cccn5)cc4c32)cc1NC(=O)CCl]

The synthesis of Compound 4 was accomplished using a procedure similar to that described in Example 1a. Exact Mass (cal.): 443.1149; MS (ESI) m/e (M+1)$^+$: 444.1871.

Example 1e

Synthesis of 2-bromo-N-(2-methyl-5-(2-oxo-9-(1H-pyrazol-1-yl) benzo[H][1,6]naphthyridin-1(2H)-yl)phenyl) acetamide 5

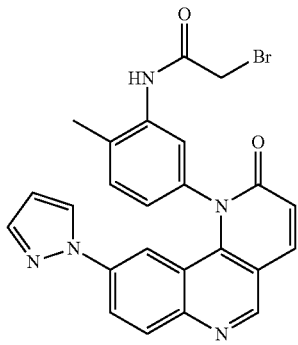 [SMILES: Cc1ccc(-n2c(=O)ccc3cnc4ccc(-n5cccn5)cc4c32)cc1NC(=O)CBr]

The synthesis of Compound 5 was accomplished using a procedure similar to that described in Example 1a. Exact Mass (cal.): 487.0644; MS (ESI) m/e (M+1)$^+$: 488.0871.

Example 1f

Synthesis of 2-iodo-N-(2-methyl-5-(2-oxo-9-(1H-pyrazol-1-yl)benzo[H][1,6]naphthyridin-1(2H)-yl)phenyl)acetamide 6

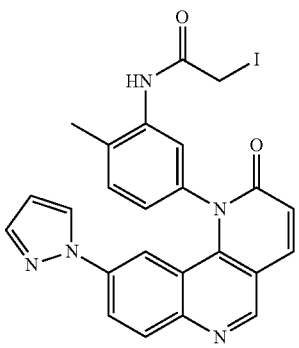 [SMILES: Cc1ccc(-n2c(=O)ccc3cnc4ccc(-n5cccn5)cc4c32)cc1NC(=O)CI]

The synthesis of Compound 6 was accomplished using a procedure similar to that described in Example 1a. Exact Mass (cal.): 535.0505; MS (ESI) m/e (M+1)$^+$: 536.0582.

Example 1g

Synthesis of (E)-4-(dimethylamino)-N-(2-methyl-5-(2-oxo-9-(1H-pyrazol-1-yl)benzo[h][1,6]naphthyridin-1(2H)-yl)phenyl)but-2-enamide 2

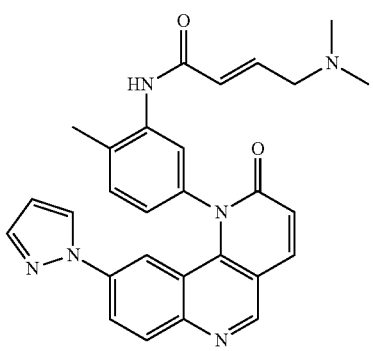 [SMILES: Cc1ccc(-n2c(=O)ccc3cnc4ccc(-n5cccn5)cc4c32)cc1NC(=O)/C=C/CN(C)C]

The synthesis of Compound 2 was accomplished using a procedure similar to that described in Example 1a. Exact Mass (cal.): 478.2117; MS (ESI) m/e (M+1)$^+$: 479.2131.

Example 1h

Synthesis of N-(2-methyl-5-(2-oxo-9-(1H-pyrazol-1-yl)benzo[H][1,6]naphthyridin-1(2H)-yl)phenyl) ethenesulfonamide 15

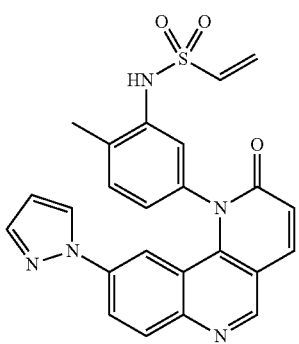 [SMILES: C=CS(=O)(=O)Nc1cc(-n2c(=O)ccc3cnc4ccc(-n5cccn5)cc4c32)ccc1C]

The synthesis of Compound 15 was accomplished using a procedure similar to that described in Example 1a. Exact Mass (cal.): 457.1209; MS (ESI) m/e (M+1)$^+$: 458.1228.

Example 1i

Synthesis of N-(2-methyl-5-(2-oxo-9-(1H-pyrazol-1-yl)benzo[H][1,6]naphthyridin-1(2H)-yl)phenyl) propionamide 19

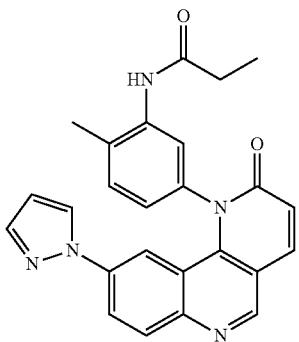 [SMILES: CCC(=O)Nc1cc(-n2c(=O)ccc3cnc4ccc(-n5cccn5)cc4c32)ccc1C]

The synthesis of Compound 19 was accomplished using a procedure similar to that described in Example 1a. Exact Mass (cal.): 423.1695; MS (ESI) m/e (M+1)$^+$: 424.1718.

Example 2: Btk In Vitro Inhibition Activity and Verification of Irreversibility The Btk IC$_{50}$ of compounds disclosed herein was determined in an acellular kinase assay as described below.

Figure 3:
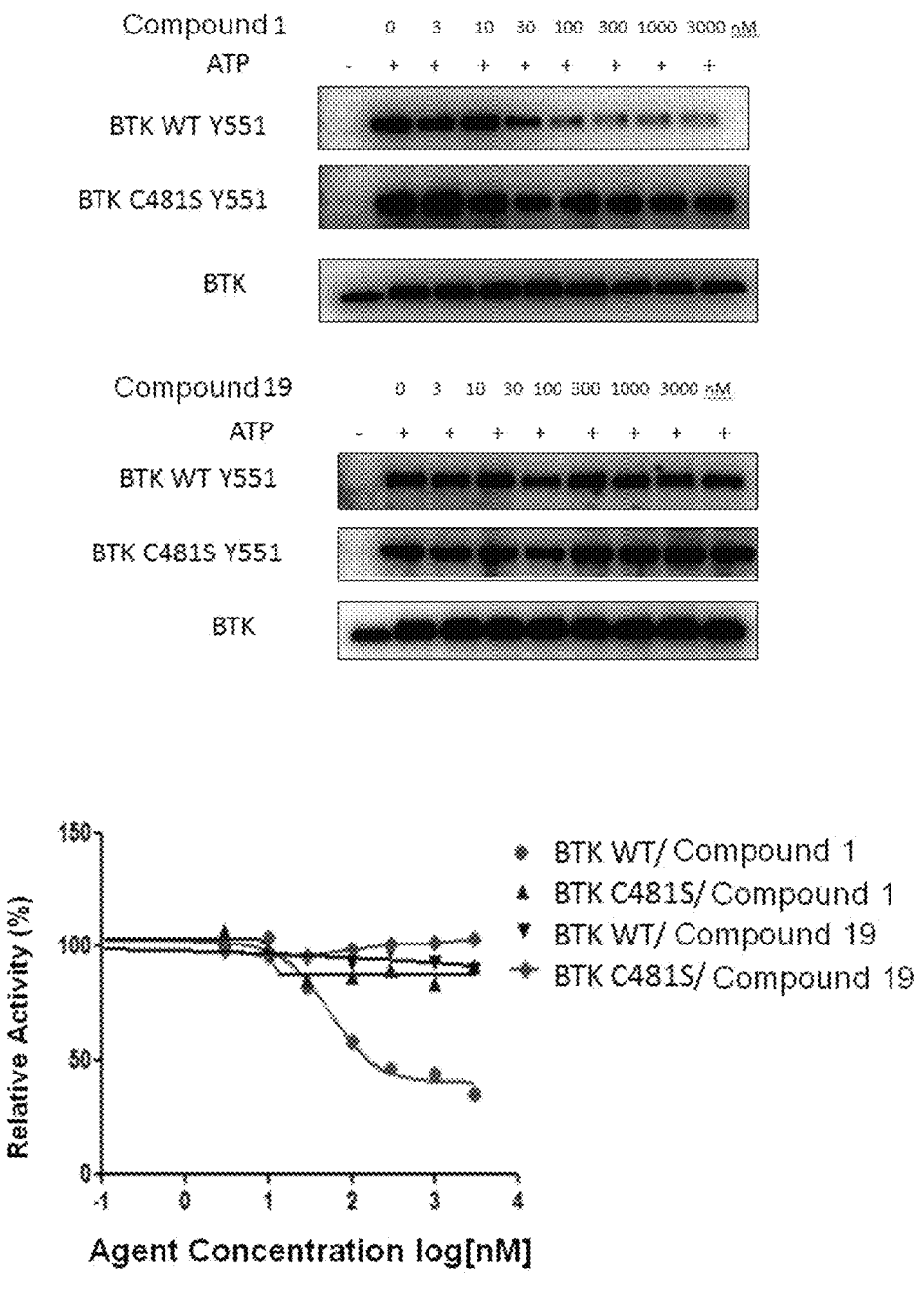
FIG. 3 illustrates the verification result of the irreversibility of Compound 1.

The BTK wild-type plasmid and the BTK mutant plasmid (C481S) were respectively transfected into 293T cells (purchased from ATCC), and the resultant cells were marked as BTK WT 293T cells and BTK C481S 293T cells, respectively. After cell culture for 2 days, the cells were harvested and purified to give BTK WT and BTK C481S proteins. The compounds of formula (I) were added to the BTK WT and BTK C481S proteins at different concentrations of 3 nM, 10 nM, 30 nM, 100 nM, 300 nM and 1000 nM, respectively, and reacted at room temperature for 30 min, followed by the addition of 100 μM ATP at 37° C. and reacting for 20 min. In some embodiments, for example, Compound 1 only has an inhibitory effect on BTK WT protein with an IC$_{50}$ of 56 nM, but has no inhibition to BTK C481S, as shown in FIG. 3; Compound 19 (differs from Compound 1 only in the terminal single bond) has no inhibitory effect on both BTK WT and BTK C481S, indicating that Compound 1 is an irreversible inhibitor of BTK (FIG. 3).

Figure 2:
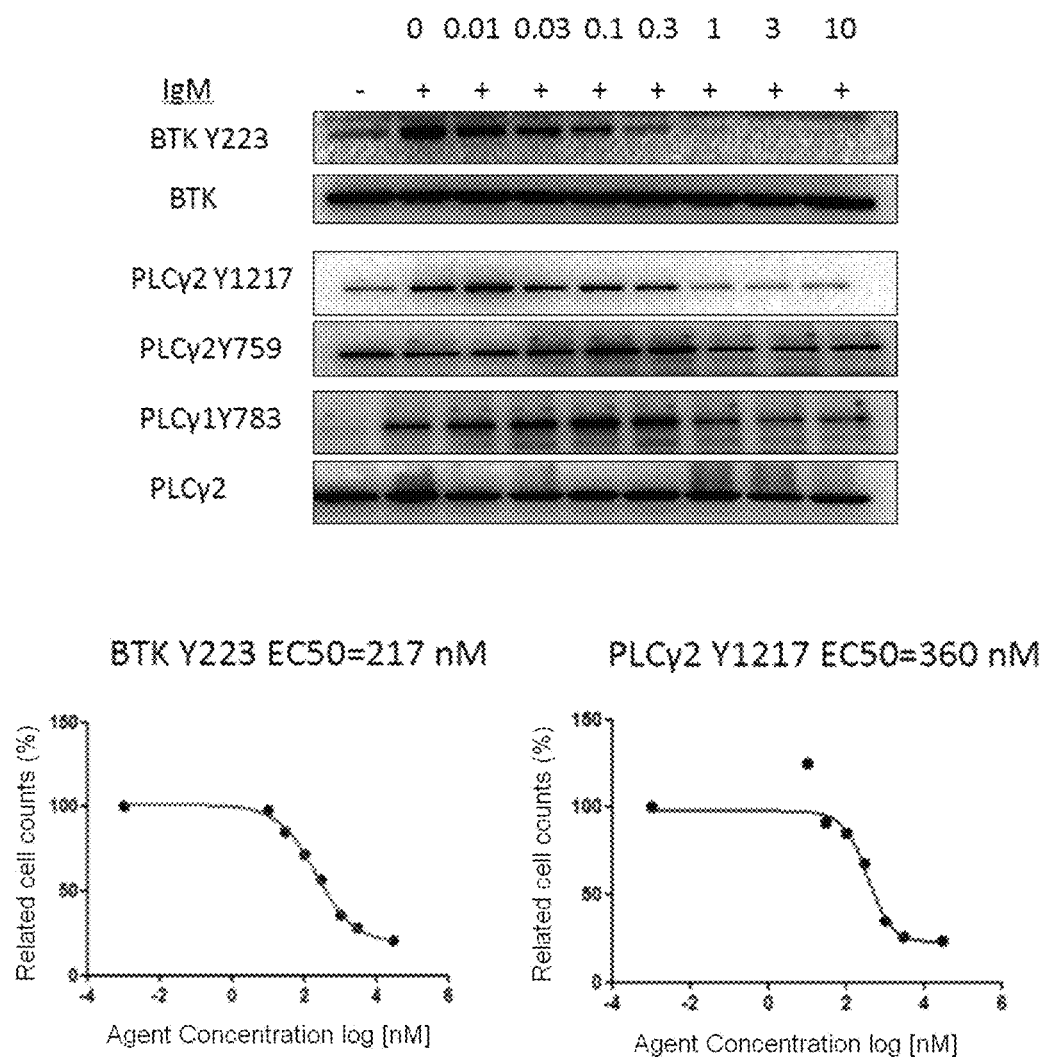
FIG. 2 illustrates the effect of Compound 1 on BTK Y223 and its downstream signaling pathways in Ramos cells.

Example 3: Effects of Btk Inhibitors on Upstream and Downstream Signaling Pathway in Cells We further characterized the properties of the compounds by assaying a number of cellular biochemical and functional endpoints. In particular, we assessed the selectivity of Compound 1 for inhibition of Btk versus the closely related protein kinases S6K, AKT, ErK, JAK3, and STAT5. Ramos cells (human B cells, purchased from ATCC) were treated with different concentrations of 10 nM, 100 nM, 1000 nM of the compounds of formula (I) for 4 hrs, followed by stimulation with anti-IgM for 10 min, and then the samples were harvested. We determined the effect of compounds on phosphorylation of BTKY223, PLCγ1Y783, PLCγ2Y759, PLCγ2Y1217, AKTT308, Erk1/2T202/204, JAK3 T980/981, STAT5 T694, mTORC1T389, MNK2 (FIG. 1). The results show that Compound 1 can selectively inhibit the phosphorylation of PLCγ2Y1217 with an EC$_{50}$ of 0.36 μM, while the phosphorylation of tyrosine Y223 on Btk can be significantly inhibited with an EC$_{50}$ of 0.217 μM (FIG. 2).

Example 4: Effect of Btk Inhibitor on Growth of Cancer Cell

We further assessed the selectivity of Compound 1 to inhibit the proliferation of cancer cells, by testing the effect of Btk inhibitor on the growth of cancer cells. In the example, we used B-lymphoma cell Ramos, cervical cancer cells HeLa, prostate cancer cells DU145, RV-1 and C4-2, colon cancer cells HCT116, blood cancer cells K562, B-cell lymphoma cells U2932, diffuse large B-cell lymphoma cells OCI-LY10, diffuse histiocytic lymphoma cells SU-DHL-2, diffuse large B-cell lymphoma cells TMD8, human non-small cell lung cancer cells H1975 (expressing EGFR L858R/T790M double mutant gene), human lung adenocarcinoma cells A549 (expressing wild-type EGFR gene), human non-small cell lung cancer cells H460 (expressing wild-type EGFR gene), mantel cell lymphoma (MCL) cells Z-138, EB virus infected human peripheral lymphocyte cells JVM-2, MCL cells REC-1, leukemia cells AML-3, acute promyelocytic leukemia cell line NB-4(Lu+), MDS-RAEB (myelodysplastic syndrome-excessive blasts) cell line SKM-1 human leukemia cell Nomo-1, human B-cell leukemia cell line NALM6, human leukocyte leukemia cells HEL, human T-cell lymphoma cells PF-382, acute myelocytic leukemia (AML) cell line MOLM14, AML cell line MOLM13, human Burkitt's lymphoma cells Namalwa, mouse pro-B cells BaF3, all of where were purchased from ATCC. Also used were mouse TEL-EGFR-BaF3 (stably expressing TEL-EGFR activated kinase), mouse TEL-EGFR/T790-BaF3 cells (stably expressing TEL-EGFR-T790M activated mutant kinase), mouse TEL-EGFR/L858R-BaF3 cells (stably expressing TEL-EGFR-L858R activated mutant kinase), mouse TEL-EGFR/T790/L858R-BaF3 (stably expressing TEL-EGFR-T790M/L858R activated mutant kinase), mouse TEL-BMX-BaF3 cells (stably expressing TEL-BMX activated kinase), mouse TEL-JAK1-BaF3 cells (stably expressing TEL-JAK1 activated kinase), mouse TEL-JAK2-BaF3 cells (stably expressing TEL-JAK2 activated kinase), mouse TEL-JAK3-BaF3 cells (stably expressing TEL-JAK3 activated kinase), where were all established by our laboratory via the following method: the kinase domain sequences of human EGFR, BMX, JAK1, JAK2, JAK3 were amplified respectively by PCR, and these kinase were inserted into the MSCV-Puro vectors with N-terminal TEL segment (Clontech); if there was a mutation, the mutation of the corresponding site was conducted by Site-Directed Mutagenesis kit (Stratagene); the resultants were stably transfected into mouse BaF3 cells by the means of retrovirus, and the IL-3 growth factors were removed, and eventually the EGFR, BMX, JAK1, JAK2, JAK3-transferred protein dependent cell lines were obtained.

In the example, different concentrations (0.000508 μM, 0.00152 μM, 0.00457 μM, 0.0137 μM, 0.0411 μM, 0.123 μM, 0.370 μM, 1.11 μM, 3.33 μM, 10 μM) of Compound 1 and Compound 19 were added into above cells, and were incubated for 72 hrs. The number of viable cells was determined by quantitating ATP in viable cells using Cell Titer-Glo® (Promega, U.S.) chemiluminescence cell viability assay kit. It was found that Compound 1 had a significant inhibition effect on the cell growth of acute myelocytic leukemia (AML) cell line MOLM13, with an $IC_{50}$ of 0.59 μM (see Table 3 below); Compound 1 also had a strong inhibition effect on the cell growth of B-cell lymphoma cell U2932, with an $IC_{50}$ of 1.15 μM, indicating that the compounds of invention have selectivity in the treatment of B-cell lymphoma.

TABLE 3

Half inhibitory concentration IC50 of Compound 1 in related cell lines

| Cell Lines | Compound 1 IC50 (μM) | Compound 19 IC50 (μM) |
|---|---|---|
| Ramos | >10 | >10 |
| HeLa | >10 | >10 |
| DU145 | >10 | >10 |
| RV-1 | >10 | >10 |
| U2932 | 1.15 | >10 |
| HCT116 | >10 | >10 |
| C4-2 | >10 | >10 |
| BaF3 | 4.2 | >10 |
| K562 | >10 | >10 |
| OCI-LY10 | >10 | >10 |
| SU-DHL-2 | 5.023 | >10 |
| TMD8 | 3.431 | >10 |
| H1975 | 3.805 | >10 |
| A549 | 3.76 | >10 |
| H460 | >10 | >10 |
| Z-138 | 8.5 | >10 |
| JVM-2 | 3.4 | >10 |
| REC-1 | 1.6 | >10 |
| AML-3 | 7.3 | >10 |
| NB-4(Lu+) | 3.7 | >10 |
| SKM-1 | 1.5 | >10 |
| Nomo-1 | 4.9 | >10 |
| NALM6 | 1.17 | >10 |
| HEL | 1.8 | >10 |
| PF-382 | 3.49 | >10 |
| MOLM14 | 1.5 | >10 |
| MOLM13 | 0.59 | >10 |
| Namalwa | 4.5 | >10 |
| TEL-EGFR-BaF3 | 2.657 | >10 |
| TEL-EGFR/T790-BaF3 | 0.9182 | >10 |
| TEL-EGFR/L858R-BaF3 | 0.292 | >10 |
| TEL-EGFR/T790/L858R-BaF3 | 1.593 | >10 |
| BaF3 | 4.278 | >10 |
| TEL-BMX-BaF3 | 0.018 | >10 |
| TEL-JAK1-BaF3 | 1.597 | >10 |

TABLE 3-continued

Half inhibitory concentration IC50 of Compound 1 in related cell lines

| Cell Lines | Compound 1 IC50 (μM) | Compound 19 IC50 (μM) |
|---|---|---|
| TEL-JAK2-BaF3 | 2.1 | >10 |
| TEL-JAK3-BaF3 | 2.3 | >10 |

Example 5: Experimental Investigation of In Vitro Enzymatic Activity of BTK Inhibitors (ATP-Glo Kit)

In the experimental assay of in vitro enzymatic activity, the IC50 values of Compound 1 and Compound 19 on different kinases including BTK, EGFR (WT), EGFR/T790M, EGFR L858R/T790M, JAK1, JAK2, and JAK3 were determined. The intracellular segment (699-1068) region of EGFR was cloned into the insect expression vector pAcG2T, and was protein expressed by using an insect expression system, BaculoGold™ Baculovirus Expression System (BD Pharmingen), with GST tag. The mutations of T790M and L858R sites were performed simultaneously to give T790M single mutant vector and T790M/L858R double mutant vector of EGFR, respectively. The established vectors were transfected into SF9 packaging viruses, so as to infect the SF9-expressed proteins with the viruses; JAK1 and JAK2 were purchased from Life Technologies (US) and Abcam (US), respectively; JAK3 and BTK were purchased from Progema (US).

BTK protein kinase 9 μL (concentration of 1.5 ng/μL), JAK1, JAK2, JAK3 protein kinases 9 μL (concentration of 3 ng/μL, 3 ng/μL, 1.5 ng/μL), purified EGFR (WT), EGFR (T790M), EGFR (T790M/L858R) protein kinases 9 μL (all with concentration of 6 ng/μL) were respectively used, and each was reacted with three-fold gradient dilution of pharmaceutical Compound 1 and Compound 19 (final concentrations of the agents were 10 μM, 3 μM, 1 μM, 0.3 μM, 0.1 μM, 0.03 μM, 0.01 μM, 0.003 μM), respectively, at room temperature for 4 hrs;

2 μL of ATP and 3 μL of substrate, Poly(4:1 Glu, Tyr) Peptide (Promega, US), were added (final concentrations are 10 μM and 0.2 μg/μL, respectively), and reacted at 37° C. for 1 hr;

5 μL of reacted kinase solution was added into 5 μL of ADP-Glo™ (Promega, US) and reacted at room temperature for 40 min, the kinase reaction was stopped and the remained ATP was consumed;

10 μL of kinase detection reagent was added to transfer ADP into ATP, and the newly obtained ATP was detected by using coupled luciferase/fluorescein reaction, then the IC50 values were calculated by using a plotting method based on the Envision reading.

Figure 4:
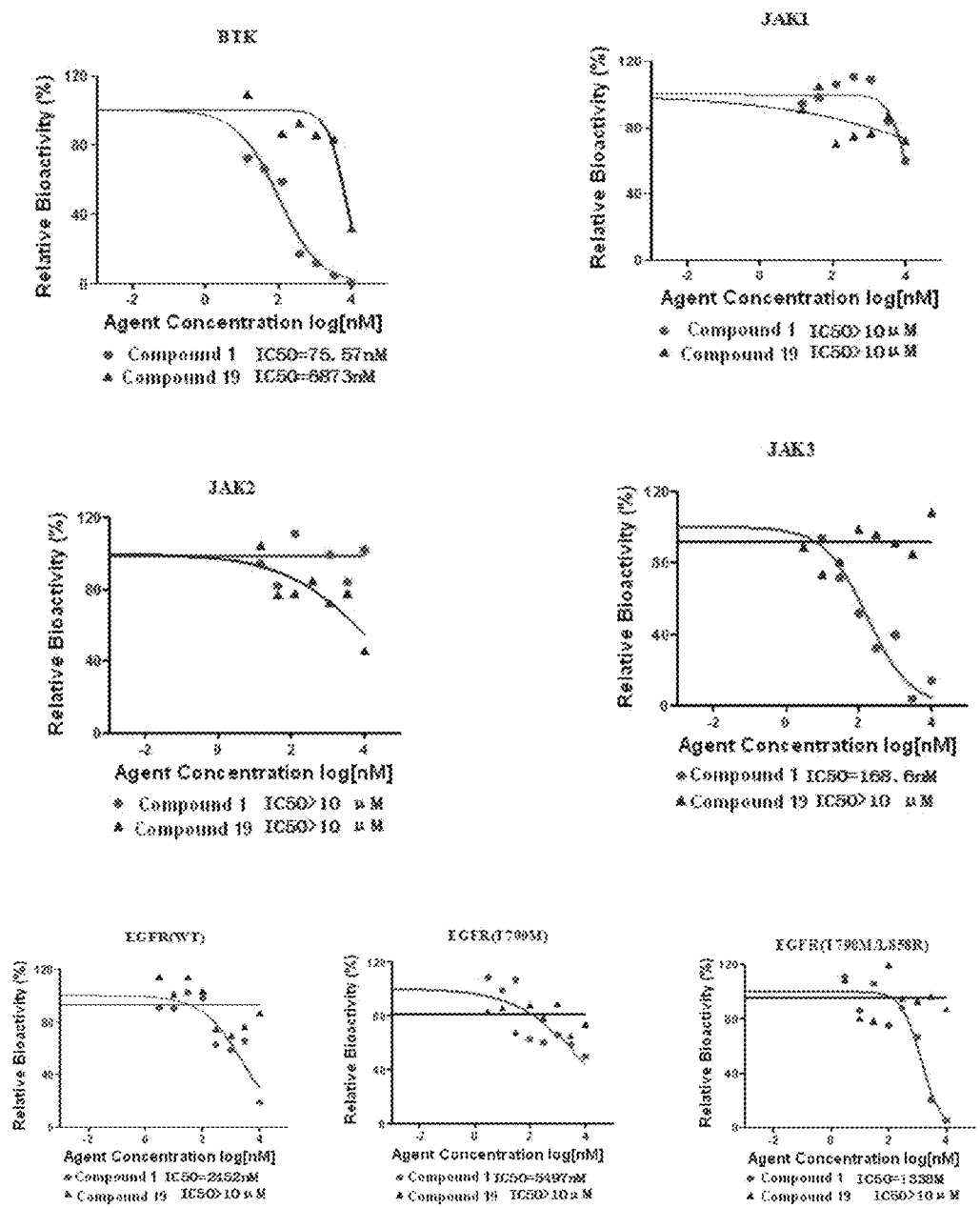
FIG. 4 illustrates the experiment results of in vitro enzymatic activity of Compound 1 and Compound 19 against BTK, JAK1, JAK2, JAK3, EGFR (WT), EGFR (T790M) and EGFR (T790M/L858R) kinases, respectively.

The experiment results were shown in FIG. 4: Compound 1 has strong inhibition effect on BTK and JAK3 proteins, with IC50 of 75.57 nM and 168.6 nM, respectively; while Compound 1 shows weaker kinase activity on EGFR (WT), EGFR (T790M), and EGFR (T790M/L858R), with IC50 of 2.452 μM, 5.497 μM and 1.338 μM, respectively. Compound 1 is a selective inhibitor of BTK, JAK3, and EGFR kinases.

Example 6: Use of Compound 1 to Treat Rheumatoid Arthritis

Rheumatoid arthritis (RA) is a chronic, systemic autoimmune disease characterized by joint synovitis as the major pathological manifestation. During the onset of the disease, the joint synovium is first affected. Under the stimulation of a variety of inflammatory factors, the tumor-like proliferation of the joint synovium, neovascularization, joint capsule thickening, joint effusion and synovial capsule effusion are occurred, resulting in the formation of pannus on the proliferated synovial surface, which gradually extends to the articular surface and the articular cartilage and erodes the same, and ultimately damages the joint cartilage and the subchondral bone, leading to joint deformity and disfunction. The etiology of RA is unknown, and the pathological mechanism is complicated, and thus, there is no ideal, safe and efficient treatment method.

In this example, SD rat adjuvant arthritis (AA) model (purchased from the Experimental Animal Center of Anhui Province) was used. PCI-32765 and methotrexate (MTX) were used as positive control (both purchased from Shanghai Chemexpress). The therapeutic effect of Compound 1 on AA rats was studied via the combination of in vivo and in vitro administration. 10 mg/nal of complete Freund's adjuvant (CFA, purchased from Shanghai Chemexpress) was mixed well, and 0.1 ml of CFA was intracutaneously injected into each rat at right posterior plantar to induce inflammation. The normal group was injected with saline via the same method. On the 17th day, the successful modeling male SD rats were randomly divided into 7 groups with 10 rats in each group, namely the model group, the small/medium/large dose of Compound 1 group (12.5, 25, 50 mg/kg/per administration, intraperitoneal injection, one administration per day for 16 days), the Compound 19 group (25 mg/kg/per administration, intraperitoneal injection, one administration per day for 16 days), the positive control PCI-32765 group (25 mg/kg/per administration, intraperitoneal injection, one administration per day for 16 days), the MTX group (0.5 mg/kg, intragastrical, one administration every 3 days, totally 6 times). The rats in the model group were intraperitoneally injected with the same amount of DMSO solution.

Figure 5:
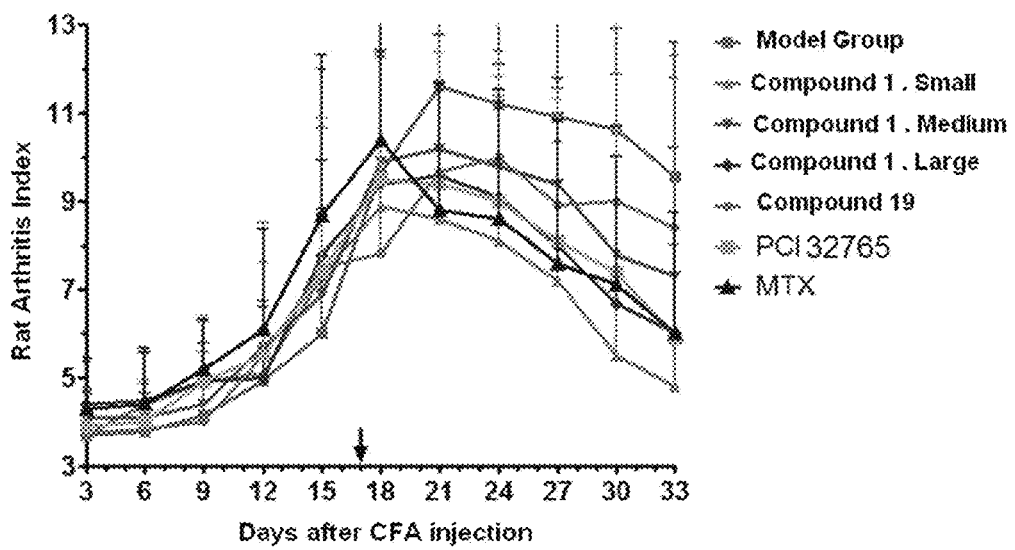
FIG. 5 illustrates the effect of Compound 1 and Compound 19 on the rat adjuvant arthritis index.

The experimental results were shown in FIG. 5. Starting from day 15, the arthritis index of the model rats was significantly increased; on day 21, it reached the peak, and then reduced. Starting from day 21, Compound 1 (12.5 mg/kg) and MTX (0.5 mg/kg) significantly reduced the arthritis index of rats, as compared with the model group; starting from day 24, Compound 1 (12.5 mg/kg) and PCI-32765 (25 mg/kg) can also significantly reduce the arthritis index of rats. Compound 19 had little effect on the rat arthritis index, indicating that Compound 1 of the present invention can significantly reduce the arthritis index of rats.

Example 7: Effects of Compound 1 on BTK in PBMC Cells

Figure 6:
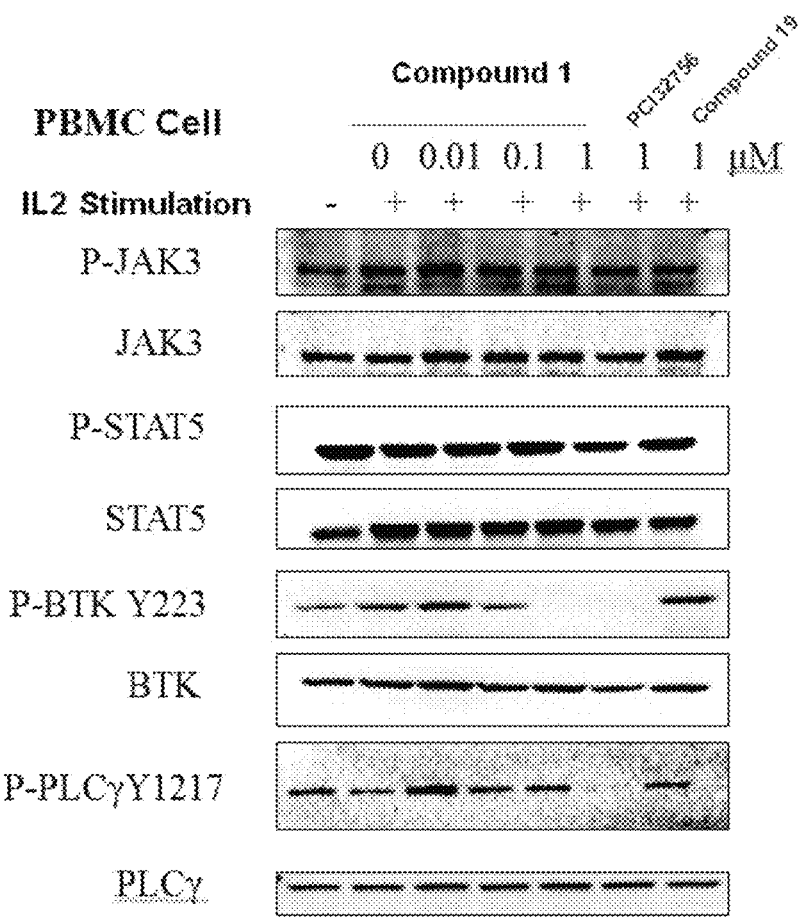
FIG. 6 illustrates the effect of Compound 1 and Compound 19 on BTK in PBMC cell.

In order to test the effect of Compound 1 on human cells, a peripheral blood mononuclear cell (PBMC) culture system with BTK signal being activated by in vitro stimulation was introduced. The phenomena occurred in the clinical patients were simulated by stimulating PBMC of a normal human with IL2 to activate the BTK signal. PBMC cells were seeded in 6-well plate and Compound 1 of different concentrations (0, 0.01, 0.1, 1 μM), 1 μM of PCI-32765 and 1 μM of Compound 19 were added; 3.5 hours later after the administration, the samples were stimulated with 20 ng/ML IL2 for 30 min and then were collected. Western Blot assay was performed. As shown in FIG. 6, IL2 may significantly enhance the phosphorylation of BTK in PBMCs; but after the addition of Compound 1, the phosphorylation of BTK was significantly inhibited, which shows some dose-dependency. When the concentration reached 1 μM, the inhibitory effect of Compound 1 was comparative to that of the positive control, PCI-32765. The negative control Compound 19 had no effect on the phosphorylation of BTK. This again demonstrates that Compound 1 is a good BTK inhibitor, and in addition, is an irreversible inhibitor.

INDUSTRIAL APPLICABILITY

The invention provides an inhibitor of Bruton's tyrosine kinase, which can be used for inhibiting the activity of tyrosine kinase or treating a disease, disorder, or condition, which would benefit from inhibition of Bruton's tyrosine kinase. Therefore, it can be prepared as corresponding medicament and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A compound of formula (I), or a pharmaceutically acceptable salt, solvate, ester, acid, or prodrug thereof:

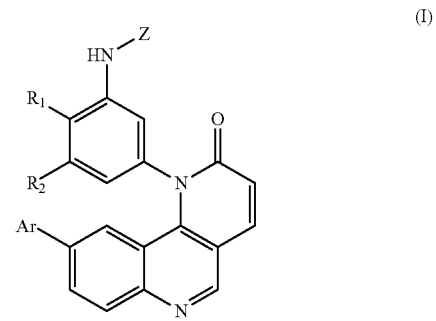

wherein, Ar is selected from the group consisting of

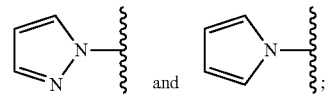 [SMILES: *n1cccn1 ; *n1cccc1]

Z is selected from the group consisting of

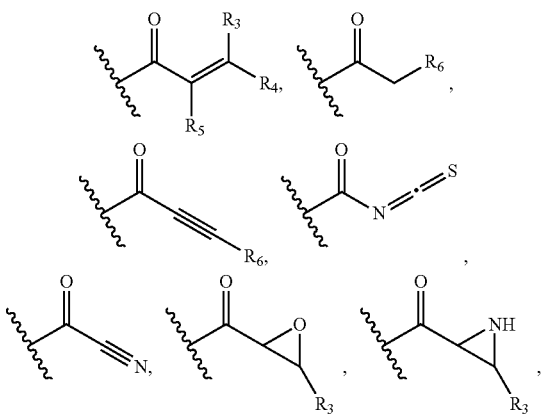

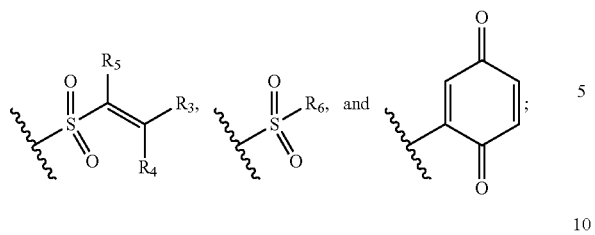

R₁ and R₂ are independently selected from the group consisting of hydrogen, halogen, $C_{1-6}$ alkyl, $C_{1-6}$ alkoxy, and $C_{1-6}$ haloalkyl;

R₃ and R₄ are independently selected from the group consisting of hydrogen, $C_{1-6}$ alkyl, $C_{1-6}$ haloalkyl, $C_{1-6}$ heteroalkyl, $C_{1-6}$ haloheteroalkyl, $C_{3-6}$ cycloalkyl, $C_{3-6}$ halocycloalkyl, $C_{2-6}$ heterocycloalkyl, $C_{2-6}$ haloheterocycloalkyl, cyano and ester groups;

R₅ is hydrogen;

R₆ is selected from the group consisting of hydrogen, halogen, diazo and $C_{1-6}$ alkyl.

2. The compound of claim 1, wherein R₁ is selected from the group consisting of hydrogen, halogen, $C_{1-4}$ alkyl, $C_{1-4}$ alkoxy, and $C_{1-4}$ haloalkyl.

3. The compound of claim 1, wherein R₂ is hydrogen.

4. The compound of claim 1, wherein R₃ and R₄ are independently selected from the group consisting of hydrogen, cyano, ester, $C_{1-4}$ haloalkyl, and $C_{1-4}$ heteroalkyl.

5. The compound of claim 1, wherein the compound is selected from the following:

1

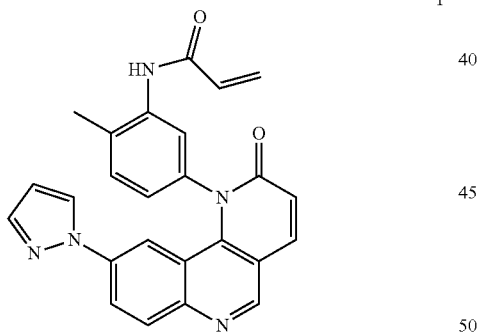

2

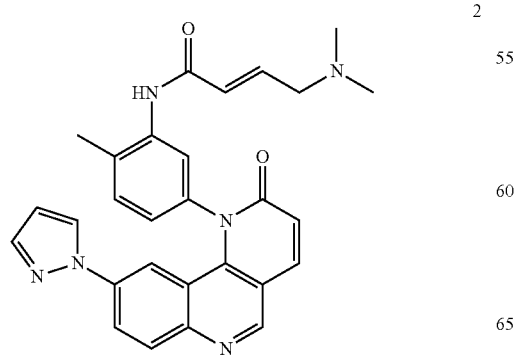

3

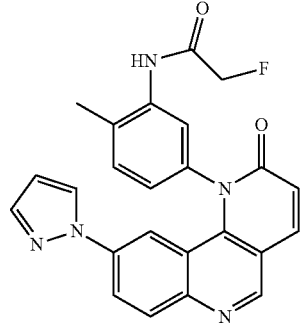

4

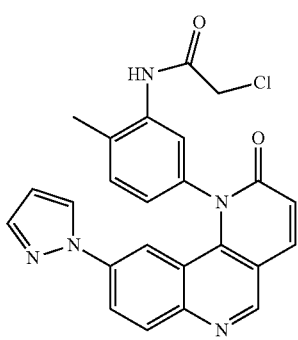

5

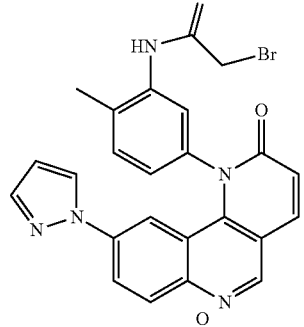

6

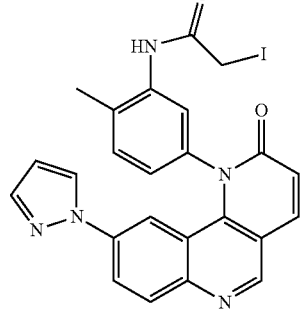

7

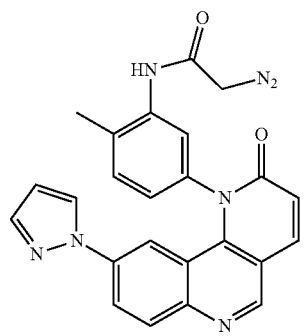

-continued
8
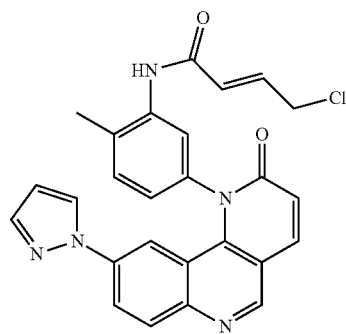
9
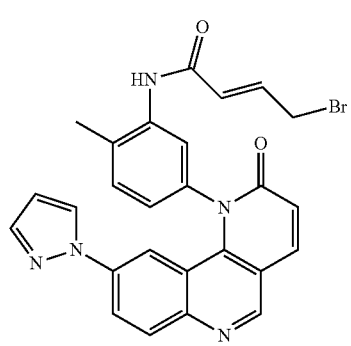
10
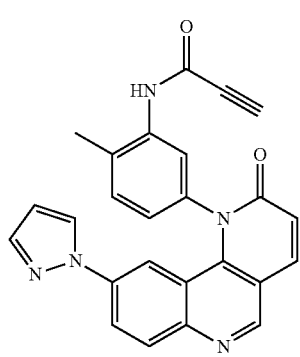
11
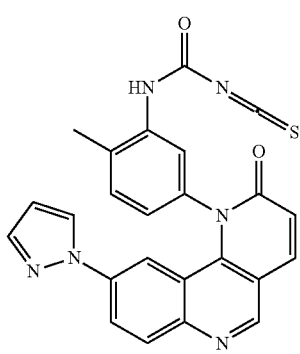
-continued
12
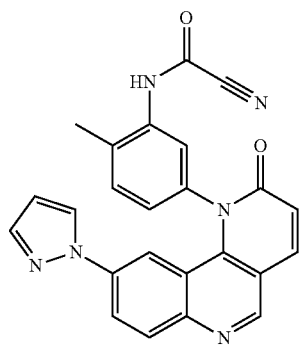
13
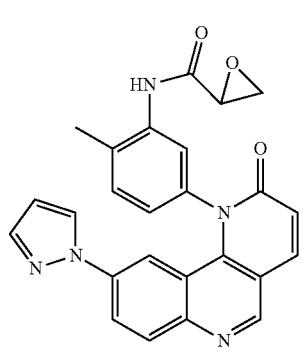
14
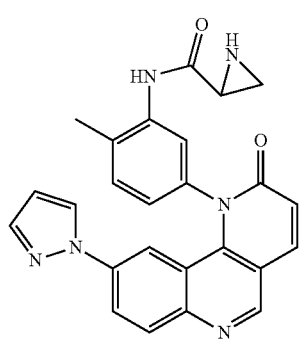
15
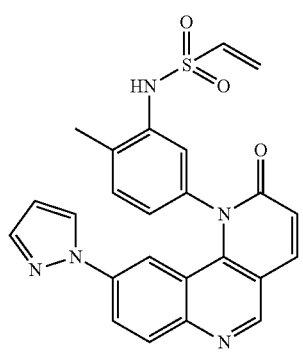

16
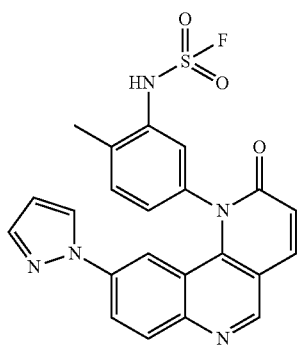
17
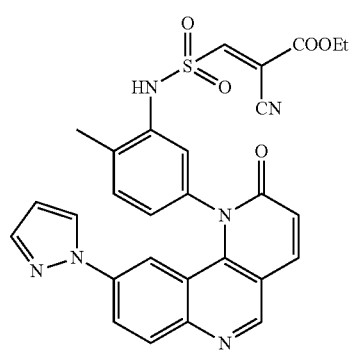
18
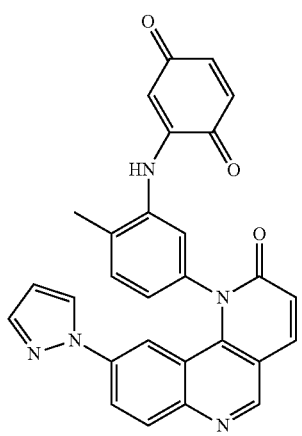
19
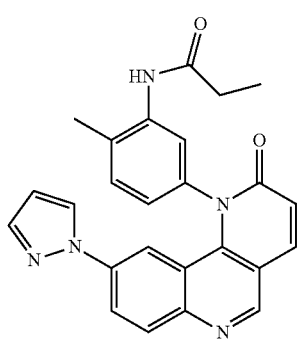
20
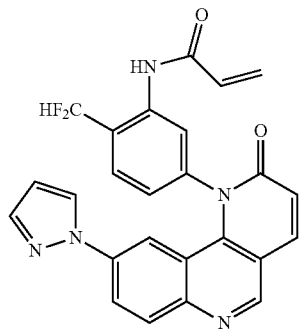
21
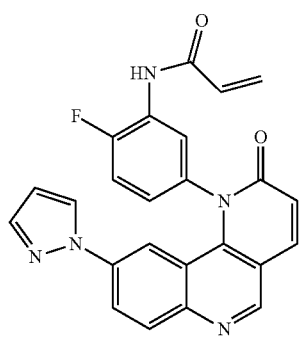
22
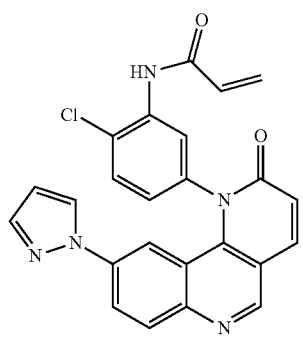
23
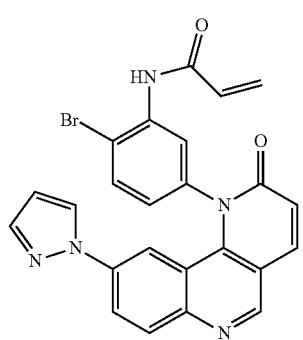

24

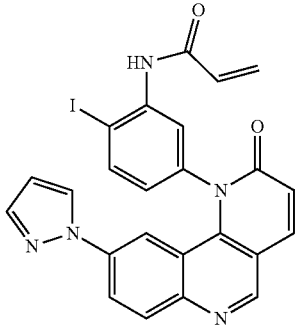

25

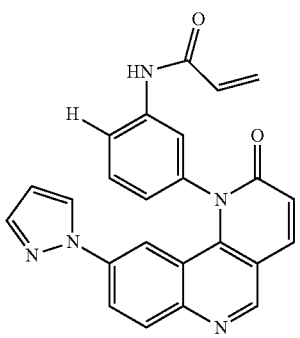

26

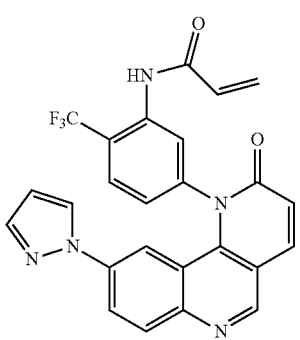

27

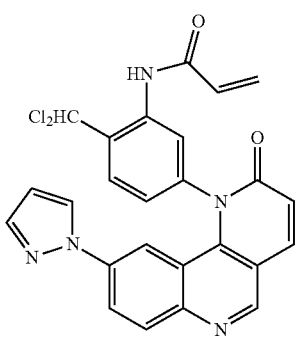

28

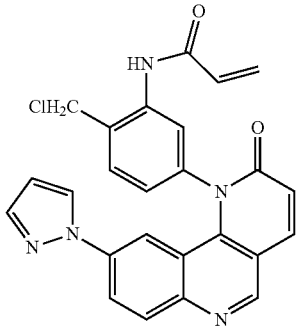

29

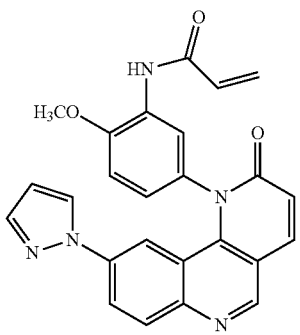

30

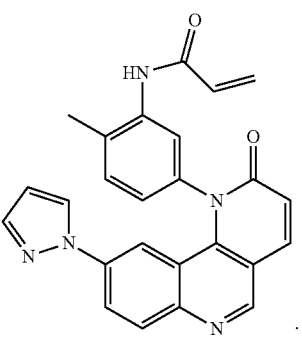

6. A pharmaceutical composition comprising the compound of claim 1, or a pharmaceutically acceptable salt, solvate, ester, acid, or prodrug thereof, and a pharmaceutically acceptable carrier or excipient, and optionally other therapeutic agents.

7. A method for the inhibition of the activity of Bruton's tyrosine kinase, comprising administering the compound of claim 1, or a pharmaceutically acceptable salt, solvate, ester, acid, or prodrug thereof, or a pharmaceutical composition comprising the compound of claim 1.

8. A method for the treatment or amelioration of a disease, disorder, or condition in a subject, which is modulated or otherwise affected by tyrosine kinase activity, or in which tyrosine kinase activity is implicated, comprising administering to the subject the compound of claim 1, or a pharmaceutically acceptable salt, solvate, ester, acid, or prodrug thereof, or a pharmaceutical composition comprising the compound of claim 1.

9. The method of claim 8, wherein the disease, disorder, or condition is cancer and/or an autoimmune disease.

10. The method of claim 9, wherein the cancer is selected from the group consisting of initiation or progression of solid tumor, B-cell lymphoma, sarcoma, lymphoma, diffuse large B-cell lymphoma, follicular lymphoma, chronic lymphocytic lymphoma, acute myeloid leukemia, chronic lymphocytic leukemia, acute lymphocytic leukemia, acute promyelocytic leukemia, chronic myeloid leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma/leukemia, lymphomatoid granulomatosis, breast ductal carcinoma, lobular carcinoma, adenocarcinoma, small cell lung cancer, non-small cell lung cancer, melanoma, or B-cell proliferative disease, or the combination thereof.

11. The method of claim 10, wherein the cancer is selected from the group consisting of acute lymphocytic leukemia, acute myeloid leukemia, acute promyelocytic leukemia, chronic lymphocytic leukemia, chronic myeloid leukemia, or B-cell proliferative disease, or the combination thereof.

12. The method of claim 11, wherein the B-cell proliferative disease is selected from the group consisting of chronic lymphocytic lymphoma, diffuse large B-cell lymphoma, follicular lymphoma, or chronic lymphocytic leukemia, or the combination thereof.

13. The method of claim 9, wherein the autoimmune disease is selected from the group consisting of arthritis, rheumatic arthritis, osteoarthritis, lupus, rheumatoid arthritis, inflammatory bowel disease, psoriatic arthritis, osteoarthritis, Still's disease, juvenile arthritis, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myoclonus syndrome, ankylosing spondylosis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia, or the combination thereof.

* * * * *